US007622631B2

(12) United States Patent
Mori et al.

(10) Patent No.: US 7,622,631 B2
(45) Date of Patent: Nov. 24, 2009

(54) METHODS FOR ENHANCING PLANT RESISTANCE TO PATHOGENS

(75) Inventors: Masaki Mori, Tsukuba (JP); Kazuhiko Sugimoto, Tsukuba (JP); Hirohiko Hirochika, Tsukuba (JP); Shoshi Kikuchi, Tsukuba (JP); Nagao Hayashi, Tsukuba (JP); Hirokazu Ochiai, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 222 days.

(21) Appl. No.: 11/289,185

(22) Filed: Nov. 28, 2005

(65) Prior Publication Data
US 2006/0130177 A1 Jun. 15, 2006

Related U.S. Application Data

(63) Continuation-in-part of application No. PCT/JP2004/007672, filed on May 27, 2004.

(30) Foreign Application Priority Data

May 29, 2003 (JP) ............................. 2003-153382
Mar. 12, 2004 (JP) ............................. 2004-071489

(51) Int. Cl.
C12N 15/09 (2006.01)
C12N 15/82 (2006.01)
C12N 15/29 (2006.01)
A01H 5/00 (2006.01)
A01H 5/10 (2006.01)

(52) U.S. Cl. .................. 800/279; 800/278; 800/298; 800/295; 435/320.1; 435/468; 435/430.1; 536/23.6

(58) Field of Classification Search .................. None
See application file for complete search history.

(56) References Cited

U.S. PATENT DOCUMENTS 6,274,789 B1 * 8/2001 Yano et al. .................. 800/279

OTHER PUBLICATIONS

Czernic et al., "Characterization of *hsr201* and *hsr515*, two tobacco genes preferentially expressed during the hypersensitive reaction provoked by phytopathogenic bacteria," *Plant Mol Biol*, 31:255-265 (1996).

D'Auria et al., "Characterization of an acyltransferase capable of synthesizing benzylbenzoate and other volatile esters in flowers and damaged leaves of *Clarkia breweri*," *Plant Physiol*, 130:466-476 (2002).

Dhondt et al., "Soluble phospholipase $A_2$ activity is induced before oxylipin accumulation in tobacco mosaic virus-infected tobacco leaves and is contributed by patatin-like enzymes," *Plant J*, 23:431-440 (2000).

Hennin et al., "Local and systemic resistance to fungal pathogens triggered by an AVR9-mediated hypersensitive response in tomato and oilseed rape carrying the *Cf-9* resistance gene," *Physiol Mol Plant Pathol*, 59:287-295 (2001).

Hiraga et al., "An HR-induced tobacco peroxidase gene is responsible to spermine, but not to salicylate, methyl jasmonate, and ethephon,"*Mol Plant Microbe Interact*, 13:210-216 (2000).

Kikuchi et al., "Collection, mapping and annotation of over 28,000 cDNA clones from *japonica* rice," *Science*, 301:376-379 (2003).

Ono et al., "Essential role of the small GTPase Rac in disease resistance of rice," *Proc Natl Acad Sci USA*, 98:759-764 (2001).

Pellegrini et al., "Phenylalanine ammonia-lyase in tobacco," *Plant Physiol*, 106:877-886 (1994).

Sasabe et al., "cDNA cloning and characterization of tobacco ABC transporter: *NtPDR1* is a novel elicitor-responsive gene," FEBS Letters, 518:164-168 (2002).

Suharsono et al., "The heterotrimeric G protein alpha subunit acts upstream of the small GTPase Rac in disease resistance of rice," *Proc Natl Acad Sci USA*, 99:13307-13312 (2002).

Takahashi et al., "Lesion mimic mutants of rice with alterations in early signaling events of defense," *Plant J*, 17:535-545 (1999).

Xiao et al., "Enhanced transcription of the Arabidopsis disease resistance genes *RPW8.1* and *RPW8.2* via a salicyclic acid-dependent amplification circuit is required for hypersensitive cell death," *Plant Cell*, 15:33-45 (2003).

Yin et al., "Characterizing rice lesion mimic mutants and identifying a mutant with broad-spectrum resistance to rice blast and bacterial blight," *Mol Plant Microbe Interact*, 13:869-876 (2000).

Yoda et al., "Identification of early-responsive genes associated with the hypersensitive response to tobacco mosaic virus and characterization of a WRKY-type transcription factor in tobacco plants," *Mol Genet Genomics*, 267:154-161 (2002).

* cited by examiner

*Primary Examiner*—Medina A Ibrahim
(74) *Attorney, Agent, or Firm*—Medlen & Carroll, LLP

(57) ABSTRACT

The present invention relates to methods of producing transgenic plants having resistance to blast fungus and/or leaf-blight bacteria by transforming the plants with a DNA encoding a protein that induces hypersensitive reaction-like lesion mimic, and transgenic plants, plant cells, seed and progeny having resistance to blast fungus and/or leaf-blight bacteria.

13 Claims, 8 Drawing Sheets

```
agagtttgttaaagtgggcgtgctatacggattcaagcaataactccacagctatggccagtacacaagtagttttggcgaaggg
tacattggtcggttcaacttgacatgggtcttttatctaaatcttatgttaagtagtaaatatttatgaccagatagaatatacat
tttcatgaaatatgctgtaactcatgaatgtccattacttttttggggccgtgcctttataagtgataaaaatcgtataattagccc
tagaaacgactgccagagtaaattctggttaatggttgaaagcatttaatattctccaagtgttacttacaggagaaaattaaacc
aatgttaattttcagatggatataaaaccgacgtatccgtgcgccaccatcaagcaagctcacatatgaaccaccgaagaacatag
atagcatcgcccaacctcgctgcattcgcattaccaaagtgtgccaacgccatggtggtgacctt cacatctcgccggagcgagcc
ggtgctgctccggccggcgaggccgacgccgcgggagacgaagcagctctccgacctcgacgaccagcggacgctgcggtactacg
agacggtggtcggcttcttccgccgatgcgacggcggcgcagctggcgccgttggcgcaccggccgacccggccaaggccatcagg
gcggcgctcgcggaggcgctggtgtactactacccgtcgccggccggctgagggaggtcgccgacggcggcggcgcggggaaccg
gctggtggtggactgcacggccgaaggggtggtgttcgtggaggccgacgccgacgtgcggctggaggacttcggccagccgctgc
tgccgccgtacccgtgcgtcggcgagctgctctgcgacgccggcgacaccagggctgtcgttggcaaaccattgctcctcatgcag
gtaacacccacgacgacgtacgtttgtttctttcatttttgtttacaatccaccactcagttaatgtttaactaacctgtctacta
tatatccgtcctaagatataaccaactaaataaaacatattttaatattacagatctgaactgtggtatatttaaattatattta
ttgtgatgtctctaatccagtattatatcgctatattttatggtggaggggtagctaaatactttattgtgttttagtgacatga
ttaatttacagtccatcttatttaccctatggattggttgtaggcatggatcaagattcattcattcgacaacaatattactttgg
ttgggtttaggttcactggtactagggaccgtgatcttaataaggattcgtaaggacgccacattgttacgagaacagtgatggta
gcttcgtgcatggttggtagggattgtacctactattaattacagcaacccactgatcttcatttacgcaagaaataatccaactt
tagatttgcagatttgattatgcacaaattagttctggagttaacaaatctcttttctgtgcaattggtttttatagtttcagttg
ccaaactgctttttcttttgaacactgccacaaacatgagaaatacaatgaatgtggcatcatattttgataacaaaaacttaaaat
acaaatacaacagccacattaactaagattttagtctgaagtagtggtgaatgggattggaccagaaaagcattgaaatggttattc
aacacaacgattagttggactggctttggggcccatcaagagggg ttccaactggagtgtgatgttgcagttggatgatatatatat
gggccggcaatattaagattgcgaattaagaatgtggtaatgttgtgttgtattattttcaatattataaaacgtttt agcttctc
catccctcatttaaattcactagcatccatatgaatttgtacagatatataaacacatatacatatgggatcaagttgcatggtcc
gactatatattcatactaacataaaaggtcggatttttcacataatactgacaatactcgagcacggaagaattcttttaatgtttt
ataagaatatatactgcctctgtttcttattctgattgagctgaccaatgtcatatagaagtgtttaggatggaggtaccatact
taccatgtctaattaattaattaatttgactgttactgatttctatatgtggcggttt cattaggtgacgcaacttaaatgcggcg
gattcgtcctgggcttccacatctgtcacaacatcgctgacggc ttcgcatggcgcagctgatcatggccatagccgacctcgca
cgtggtgagccagccccgaccattctgcccgtatggaggaggggacctactcacggcagcacgcctaggtagcggcgcggtggcacg
cacgccctttgcatcggcggcggcggcgtcggcctcggcgtcgagcccggcactacagaacggtgctcgccgcgccgccgccgcgg
ctgacgcgatgctgtcgaccccgccggaccggatggtggtggagtacttcctgttcgggccacgggaggtgtcctacctgcgtggc
cagctgccggcgcacctggcggactccaccacgcgtgttcgagctgctcaccgccgtcatgtggcggtgccgcacggcggcgctcgg
gtacgggcccgacctccgcgtccggctaatgatcaccatgaacgcgcgcgggaggtggaacgcgcacacccccgctcccgcgcggct
tctacggcaacgcgcacgtctcccccgtcgccgaggccgccgccggcgacctcctcgggcggccgctcgccgacacggtggagctc
gtgcggaggaccaagcgcgggatgacgcgggagcggatgagcgccatggtggagacggttggcgcagctgcgggagtggccgccgtc
gagcatggacagggtgtacgaggtctccgacatcaagtggaccaccgtgaacttgctcaagttcgggtgggctgagttcgccggcg
gcggcataccgctcgcaggcgatctcacctccaagctcggaagcgaccacacgaggtgcaagaactcggccggcgaggtgtcgacg
gtggtgtcgatgctgctgcccagggtggccatggcgaggttcaagaaggagatggccgttttgttgaacaaagatgacaagaagag
cttgacaattatgagttcgctgtagttgttgccacacatttcaagcaaaggttcttaaacagctaatggtcaccaaagcacatttt
tatcactgtcacttcatcatttctgatcgatctagttgtgcacatctaatttagtgggacaatcggtttacttagtggagtactac
aatatatgtaattgtattcagttgtgtctacctgttcatctgcacaggctattggatttt catcagttctttaattgtaaaataca
cccctcccttt aatgtatgcgcacatactttt aacttgtaaagttacctcgctcattatagtttgtaatgtgagcttttt ataaat
ttgtttctattacttatgacggaaaagataaaagaaaataattaaattaaactcctcttgtaacct tggagcggcctacg
```

FIG. 2

MVVTFTSRRSEPVLLRPARPTPRETKQLSDLDDQRTLRYYETVVGFFRRCDGGAAGAVGAPADPAKAIRA
ALAEALVYYYPVAGRLREVADGGGAGNRLVVDCTAEGVVFVEADADVRLEDFGQPLLPPYPCVGELLCDA
GDTRAVVGKPLLLMQVTQLKCGGFVLGFHICHNIADGFGMAQLIMAIADLARGEPAPTILPVWRRDLLTA
ARLGSGAVARTPFASAAAASASASSPALQNGARRAAAAADAMLSTPPDRMVVEYFLFGPREVSYLRGQLP
AHLADSTTVFELLTAVMWRCRTAALGYGPDLRVRLMITMNARGRWNAHTPLPRGFYGNAHVSPVAEAAAG
DLLGRPLADTVELVRRTKRGMTRERMSAMVETVAQLREWPPSSMDRVYEVSDIKWTTVNLLKFGWAEFAG
GGIPLAGDLTSKLGSDHTRCKNSAGEVSTVVSMLLPRVAMARFKKEMAVLLNKDDKKSLTIMSSL

FIG. 3

METHODS FOR ENHANCING PLANT RESISTANCE TO PATHOGENS

This application is a continuation-in-part of PCT/JP04/007672, filed May 27, 2004, which claims priority to Japanese Patent Application Nos. 2004-071489, filed Mar. 12, 2004, and 2003-153382, filed May 29, 2003.

TECHNICAL FIELD

The present invention relates to enhancement of plant resistance to pathogen invasion, such as invasion by pathogenic microorganisms and pests.

BACKGROUND ART

"Hypersensitive reaction" (HR) is a known plant resistance response against the invasion of pathogens such as pathogenic microorganisms and pests. Specifically, when a pathogen invades, plants attempt to defend themselves by rapidly causing the death of infected cells using the HR-mediated loss of cellular turgor pressure. Cell groups killed by the reaction necrotize, become brown, and form local lesions to prevent pathogen expansion. Thus, enhancing plant HR is thought to be important when breeding pathogen-resistant plants.

Lesion mimic mutants that form necrotic spots even in the absence of pathogen invasion are known to exist. Some of these mutants are plants whose resistance mechanism is constantly activated. These lesion mimic mutants include rice cdr1 to cdr3 and sp11 to sp19 (see Non-patent Documents 1 and 2).

Genes that cause spotted leaves are also thought to include genes that induce HR; however, only a few HR-inducing genes have actually been isolated. In rice, only Rac and G protein alpha subunit are known as such HR-inducing genes (see Non-patent Documents 3 and 4).

Transcription of many genes is known to be activated during HR in tobacco (see Non-patent Documents 5 to 10). Nicotiana tabacum hsr201 is reported as one such gene, and its transcription is induced by HR (Non-patent Document 6), but it is not known whether overexpression of the gene induces HR.

Non-patent Document 1: Takahashi A, Tsutomu Kawasaki, Kenji Henmi, Katsuhiko Shii, Osamu Kodama, Hikaru Satoh, Ko Shimamoto. Lesion mimic mutants of rice with alterations in early signaling events of defense. Plant J (1999) 17(5):535-545.

Non-patent Document 2: Yin Z, Chen J, Zeng L, Goh M, Leung H, Khush G S, Wang G L. Characterizing rice lesion mimic mutants and identifying a mutant with broad-spectrum resistance to rice blast and bacterial blight. Mol Plant Microbe Interact. 2000 Aug.; 13(8):869-76.

Non-patent Documents 3: Ono E, Wong H L, Kawasaki T, Hasegawa M, Kodama O, Shimamoto K. Essential role of the small GTPase Rac in disease resistance of rice. Proc Natl Acad Sci USA. 2001 Jan. 16; 98(2):759-64.

Non-patent Document 4: Suharsono U, Fujisawa Y, Kawasaki T, Iwasaki Y, Satoh H, Shimamoto K. The heterotrimeric G protein alpha subunit acts upstream of the small GTPase Rac in disease resistance of rice. Proc Natl Acad Sci USA. 2002 Oct. 1; 99(20):13307-12.

Non-patent Document 5: Pellegrini L, Rohfritsch O, Fritig B, Legrand M. Phenylalanine ammonia-lyase in tobacco. Molecular cloning and gene expression during the hypersensitive reaction to tobacco mosaic virus and the response to a fungal elicitor. Plant Physiol. 1994 November; 106(3):877-86.

Non-patent Document 6: Czemic P Huang H C, Marco Y. Characterization of hsr201 and hsr515, two tobacco genes preferentially expressed during the hypersensitive reaction provoked by phytopathogenic bacteria. Plant Mol Biol. 1996 May; 31(2):255-65.

Non-patent Document 7: Hiraga S, Ito H, Yamakawa H, Ohtsubo N, Seo S, Mitsuhara I, Matsui H, Honma M, Ohashi Y. An HR-induced tobacco peroxidase gene is responsive to spermine, but not to salicylate, methyl jasmonate, and ethephon. Mol Plant Microbe Interact. 2000 February; 13(2):210-6.

Non-patent Document 8: Dhondt S, Geoffroy P, Stelmach B A, Legrand M, Heitz T. Soluble phospholipase A2 activity is induced before oxylipin accumulation in tobacco mosaic virus-infected tobacco leaves and is contributed by patatin-like enzymes. Plant J. 2000 August; 23(4):431-40.

Non-patent Document 9: Yoda H, Ogawa M, Yamaguchi Y, Koizumi N, Kusano T, Sano H. Identification of early-responsive genes associated with the hypersensitive response to tobacco mosaic virus and characterization of a WRKY-type transcription factor in tobacco plants. Mol Genet Genomics. 2002 April; 267(2):154-61.

Non-patent Document 10: Sasabe M, Toyoda K, Shiraishi T, Inagaki Y, Ichinose Y. cDNA cloning and characterization of tobacco ABC transporter: NtPDR1 is a novel elicitor-responsive gene. FEBS Lett. 2002 May 8; 518(1-3):164-8.

DISCLOSURE OF THE INVENTION

An objective of the present invention is to provide novel agents for enhancing disease resistance or pest resistance, where the agents comprise genes encoding proteins that enhance plant resistance to pathogen invasion. Another objective of the present invention is to provide plants in which resistance is enhanced through utilization of the genes, and to provide methods for enhancing plant resistance using the genes. Still another objective of the present invention is to provide methods of screening for compounds that bind to the proteins, or compounds that enhance expression of the genes.

The present inventors conducted intensive studies, concentrating on the hypersensitive reaction among the various reactions involved in the enhancement of plant resistance. As a result, the inventors discovered genes that induce hypersensitive reaction, and thus completed the present invention.

More specifically, the present invention relates to:

(1) An agent for enhancing plant resistance to pathogens, which comprises a DNA encoding a protein with the function of enhancing plant resistance to pathogens, wherein the DNA is selected from any one of:

(a) a DNA encoding a protein comprising the amino acid sequence of SEQ ID NO: 2;

(b) a DNA encoding a protein comprising an amino acid sequence with one or more amino acid substitutions, deletions, additions, and/or insertions in the amino acid sequence of SEQ ID NO: 2; and (c) a DNA hybridizing under stringent conditions to a DNA comprising the nucleotide sequence of SEQ ID NO: 1 or to a DNA comprising the nucleotide sequence of SEQ ID NO: 3.

(2) An agent for enhancing plant resistance to pathogens, which comprises a vector comprising a DNA encoding a protein with the function of enhancing plant resistance to pathogens, wherein the DNA is selected from any one of:

(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3.

(3) A plant cell with enhanced pathogen resistance, to which a DNA encoding a protein with the function of enhancing plant resistance to pathogens has been introduced, wherein the DNA is selected from any one of:
(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3.

(4) A plant cell with enhanced pathogen resistance, to which a vector comprising a DNA encoding a protein with the function of enhancing plant resistance to pathogens has been introduced, wherein the DNA is selected from any one of:
(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3.

(5) A transformant plant with enhanced pathogen resistance, wherein said transformant plant comprises the plant cell of (3) or (4).

(6) A transformant plant with enhanced pathogen resistance, wherein said transformant plant is a progeny or clone of the transformant plant of (5).

(7) A breeding material of the transformant plant of (5) or (6).

(8) A method for producing the transformant plant of (5), which comprises the steps of introducing into a plant cell a DNA encoding a protein with the function of enhancing plant resistance to pathogens, and regenerating a plant from said plant cell, wherein said DNA is selected from any one of:
(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3.

(9) A method for enhancing plant resistance to pathogens, which comprises expressing within a cell of a plant a DNA encoding a protein with the function of enhancing plant resistance to pathogens, wherein the DNA is selected from any one of:
(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3.

(10) A method of screening for a gene whose expression is influenced by a DNA encoding a protein with the function of enhancing plant resistance to pathogens, wherein the DNA is selected from any one of:
(a) a DNA encoding a protein comprising the amino acid sequence of SEQ ID NO: 2;
(b) a DNA encoding a protein comprising an amino acid sequence with one or more amino acid substitutions, deletions, additions, and/or insertions in the amino acid sequence of SEQ ID NO: 2; and
(c) a DNA hybridizing under stringent conditions to a DNA comprising the nucleotide sequence of SEQ ID NO: 1 or to a DNA comprising the nucleotide sequence of SEQ ID NO: 3, and wherein the method comprises the steps of:
(d) introducing and expressing the DNA in a plant cell;
(e) measuring the gene expression in the plant cell; and
(f) selecting a gene whose expression levels are increased as compared with those when the gene is not expressed.

(11) A method of screening for a compound that binds to a protein selected from any one of:
(a) a protein comprising the amino acid sequence of SEQ ID NO: 2;
(b) a protein comprising an amino acid sequence with one or more amino acid substitutions, deletions, additions, and/or insertions in the amino acid sequence of SEQ ID NO: 2; and
(c) a protein encoded by a DNA hybridizing under stringent conditions to a DNA comprising the nucleotide sequence of SEQ ID NO: 1 or to a DNA comprising the nucleotide sequence of SEQ ID NO: 3;

wherein said method comprises the steps of:
(d) contacting a test compound with the protein;
(e) detecting the binding between the protein and the test compound; and
(f) selecting a compound that binds to the protein.

(12) A method of screening for a compound that increases the expression level of a gene encoding a protein selected from any one of:
(a) a protein comprising the amino acid sequence of SEQ ID NO: 2;
(b) a protein comprising an amino acid sequence with one or more amino acid substitutions, deletions, additions, and/or insertions in the amino acid sequence of SEQ ID NO: 2; and
(c) a protein encoded by a DNA hybridizing under stringent conditions to a DNA comprising the nucleotide sequence of SEQ ID NO: 1 or to a DNA comprising the nucleotide sequence of SEQ ID NO: 3;

wherein said method comprises the steps of:
(d) providing a cell or cell extract, which comprises a DNA in which a reporter gene has been operably linked downstream of a promoter region of a gene encoding the protein;
(e) contacting a test compound with the cell or cell extract;

(f) determining the expression level of the reporter gene in the cell or cell extract; and (g) selecting a compound that increases the expression level of the reporter gene as compared with a case where a compound has not been added.

The present invention provides agents for enhancing plant resistance to pathogens, where the agents comprise DNAs encoding proteins that induce the plant hypersensitive reaction.

Such DNAs include (a) a DNA encoding a protein comprising the amino acid sequence of SEQ ID NO: 2, (b) a DNA encoding a protein comprising an amino acid sequence with one or more amino acid substitutions, deletions, additions, and/or insertions in the amino acid sequence of SEQ ID NO: 2, and, (c) a DNA hybridizing under stringent conditions to a DNA comprising the nucleotide sequence of SEQ ID NO: 1 or to a DNA comprising the nucleotide sequence of SEQ ID NO: 3.

In the above description, "one or more" means 1 to 50, preferably 1 to 10, more preferably 1 to 5, still more preferably 1 to 3.

The "substitution, deletion, addition and/or insertion" are preferably a substitution, deletion, addition and/or insertion (hereinafter abbreviated as "substitution and such") at a site where protein activity is not affected. A preferred "substitution" is a conservative substitution (a substitution between amino acids with biologically equivalent functions).

In the above description, "stringent conditions" mean 6 M urea, 0.4% SDS, and 0.5×SSC, or conditions with stringencies equivalent thereto. Preferred stringent conditions are 6 M urea, 0.4% SDS, and 0.1×SSC.

The DNAs of the present invention include DNAs that encode proteins comprising the amino acid sequence of SEQ ID NO: 2, and mutants, derivatives, alleles, variants, and homologues thereof.

Herein, "DNA" refers to DNAs obtained from the natural world, such as genomic DNAs and cDNAs, and DNAs obtained by artificial synthesis. The DNAs of the present invention are preferably plant-derived DNAs, more preferably monocot-derived DNAs, still more preferably DNAs derived from plants belonging to the Gramineae family, and most preferably, rice-derived DNAs. In the above description, "derived" means obtained from a plant or such, regardless of the presence or absence of artificial alteration. For example, "plant-derived DNA" means a DNA obtained directly from a plant, or a DNA obtained by artificially altering that DNA.

Methods for artificially mutating DNAs are known to those skilled in the art. DNAs that encode proteins in which the amino acid sequence has been altered by such mutations are also included in the DNAs of the present invention, as long as the proteins encoded by the DNAs function to enhance plant resistance to pathogens.

In the natural world, physical and chemical factors such as ultraviolet light may introduce mutations into DNA nucleotide sequences, which may lead to mutations in the amino acid sequences of the proteins encoded by the DNAs. DNAs that encode proteins in which the amino acid sequence has been altered by such mutations are also included in the DNAs of the present invention, as long as the proteins encoded by the DNAs function to enhance plant resistance to pathogens.

Some of the above-described DNA nucleotide sequence mutations may not result in any mutations in the amino acid sequence of the protein encoded by the DNA (degenerate mutations). Such mutants (degenerate mutants) are also included in the DNAs of the present invention.

The DNAs described above in (c) of the present invention may have high homology to the amino acid sequence of SEQ ID NO: 2 at the amino acid level. Herein, "high homology" refers to at least 50% or higher identity throughout the entire amino acid sequence. The DNAs of the present invention are DNAs encoding amino acid sequences preferably having 70% or higher identity to the amino acid sequence of SEQ ID NO: 2, more preferably 90% or higher identity, still more preferably 95% or higher identity, particularly preferably 97% or higher identity, most preferably 99% or higher identity.

The amino acid sequence or nucleotide sequence "identity" described above can be determined based on the BLAST algorithm of Karlin and Altschul (Proc. Natl. Acad. Sci. USA 90:5873-5877, 1993). Based on this algorithm, programs called "BLASTN" and "BLASTX" have been developed (Altschul et al. J. Mol. Biol. 215:403-410, 1990). When a nucleotide sequence is analyzed by BLAST-based BLASTN, the nucleotide sequence identity can be analyzed, for example, using the following parameters: score=100 and wordlength=12. When an amino acid sequence is analyzed by BLAST-based BLASTX, the amino acid sequence identity can be analyzed for example, using the following parameters: score=50 and wordlength=3. When the BLAST or Gapped BLAST program is used, analysis may be achieved using the default parameters for each program. Specifically, these analyses can be achieved using conventional methods (http://www.ncbi.nlm.nih.gov/).

The DNAs of the present invention include, for example, DNAs (hereinafter sometimes referred to as the "AAM97746.1 gene") that encodes the protein of SEQ ID NO: 2 (hereinafter sometimes referred to as "AAM97746.1 protein"), such as those comprising the nucleotide sequence of SEQ ID NO: 1 or 3;

DNAs (hereinafter sometimes referred to as the "BAC65990.1 gene") that encodes the protein of SEQ ID NO: 5 (hereinafter sometimes referred to as "BAC65990.1 protein"), such as those comprising the nucleotide sequence of SEQ ID NO: 4 or 6;

DNAs (hereinafter sometimes referred to as the "AAG12479.2 gene") that encodes the protein of SEQ ID NO: 8 (hereinafter sometimes referred to as "AAG12479.2 protein"), such as those comprising the nucleotide sequence of SEQ ID NO: 7 or 9;

DNAs (hereinafter sometimes referred to as the "AAG12486.2 gene") that encodes the protein of SEQ ID NO: 11 (hereinafter sometimes referred to as "AAG12486.2 protein"), such as those comprising the nucleotide sequence of SEQ ID NO: 10 or 12;

DNAs (hereinafter sometimes referred to as the "AAL75750.1 gene") that encodes the protein of SEQ ID NO: 14 (hereinafter sometimes referred to as "ALL75750.1 protein"), such as those comprising the nucleotide sequence of SEQ ID NO: 13 or 15;

DNAs (hereinafter sometimes referred to as the "AAG12484.2 gene") that encodes the protein of SEQ ID NO: 17 (hereinafter sometimes referred to as "AAG12484.2 protein"), such as those comprising the nucleotide sequence of SEQ ID NO: 16 or 18; and DNAs (hereinafter sometimes referred to as the "AAG12478.2 gene") that encodes the protein of SEQ ID NO: 20 (hereinafter sometimes referred to as "AAG12478.2 protein"), such as those comprising the nucleotide sequence of SEQ ID NO: 19 or 21.

Of these, the AAM97746.1, BAC65990.1, AAG12479.2, AAG12486.2, AAL75750.1, AAG12484.2, and AAG12478.2 genes are preferable. More preferable is the AAM 97746.1 gene; and still more preferable are DNAs comprising the nucleotide sequence of SEQ ID NO: 1 or SEQ ID NO: 3.

Herein, the phrase "with the function of enhancing plant resistance to pathogens" means having the function of enhancing plant resistance to pathogen invasion, such as invasion by pathogenic microorganisms and pests, and specifically, it means the function of enhancing the plant hypersensitive reaction at the time of pathogen invasion, such as an invasion by pathogenic microorganisms or pests. It is possible to judge whether a protein has such a function or not, for example, by observing the formation of lesions on plant leaves or the expression of pathogen-related (hereinafter referred to as "PR") proteins according to the methods described below.

The "agent" refers to a DNA or vector of the present invention, or a composition comprising a DNA or vector of the present invention. The "composition" in the above description may comprise various substances. There is no limitation on such substances, as long as they allow for the composition to achieve the purpose of the present invention. Such substances include, for example, substances that stabilize DNAs or vectors, substances that help to introduce DNAs or vectors into plant cells, and substances that increase the total volume to enable easy quantification of DNAs or vectors.

The "plant cell" may be any form of plant cell, without limitation on the form. The cells include, for example, suspension culture cells, protoplasts, leaf pieces, and calluses.

The "breeding material" refers to plants (plant cells) in a form that can serve as materials for plant breeding. The materials include, for example, seeds, fruits, cut panicles, tubers, tuberous roots, stumps, calluses, and protoplasts.

The present invention includes all plant cells into which a DNA of the present invention has been introduced, plants comprising these cells, progenies and clones thereof, and breeding materials comprising the plants and progenies or clones thereof.

(I) Preparation of the DNAs

Genomic DNAs and cDNAs can be prepared by methods known to those skilled in the art.

The genomic DNAs can be prepared, for example, by the following procedure: a genomic library (plasmid, phage, cosmid, BAC, PAC, or such can be used as a vector) is prepared using genomic DNAs extracted from a rice variety with the AAM97746.1 gene (for example, Kasalath or Nipponbare, preferably Nipponbare). The library is then developed, and colony or plaque hybridization is carried out using a probe prepared based on a DNA encoding a protein of the present invention (for example, a DNA comprising the nucleotide sequence of SEQ ID NO: 1 or 3). Alternatively, genomic DNAs can be prepared by preparing primers specific to a DNA encoding a protein of the present invention (for example, a DNA comprising the nucleotide sequence of SEQ ID NO: 1 or 3) and carrying out PCR using the primers.

The cDNAs can be prepared, for example, by the following procedure: cDNAs are synthesized from mRNAs extracted from a rice variety with the AAM97746.1 gene (for example, Kasalath or Nipponbare, preferably Nipponbare) and inserted into a vector such as λ ZAP, to prepare a cDNA library. The library is then developed and colony hybridization, plaque hybridization, or PCR as described above is used to produce cDNAs.

DNAs encoding proteins with an altered amino acid sequence can be prepared by methods well known to those skilled in the art. For example, the DNAs can be prepared by site-directed mutagenesis, as described in Kramer, W. & Fritz, H.-J. ((1987) Oligonucleotide-directed construction of mutagenesis via gapped duplex DNA. Methods in Enzymology, 154: 350-367).

When preparing DNAs encoding proteins with the function of enhancing plant resistance to pathogens, alternative methods well known to those skilled in the art include method using hybridization (Southern, E. M. (1975) Journal of Molecular Biology, 98, 503) or polymerase chain reaction (PCR) (Saiki, R. K. et al. (1985) Science, 230, 1350-1354; Saiki, R. K. et al. (1988) Science, 239,487-491). DNAs highly homologous to the AAM97746.1 gene can be isolated from rice or other plants, for example, by carrying out hybridization using the nucleotide sequence of the AAM97746.1 gene (SEQ ID NO: 1 or 3) or a portion thereof as a probe, according to methods known to those skilled in the art, or by carrying out PCR using oligonucleotides that hybridize specifically to the AAM97746.1 gene (SEQ ID NO: 1 or 3) as primers. DNAs thus-isolated by hybridizations or PCR methods are also included in the DNAs of the present invention, as long as the proteins encoded by the DNAs have the function of enhancing plant resistance to pathogens.

When DNAs are isolated using the hybridization methods described above, the hybridization reaction is carried out preferably under stringent conditions.

(II) Methods for Creating Transformant Plants

The DNAs of the present invention can be used, for example, to create transformant plants with enhanced pathogen resistance. Such transformant plants can be created by inserting a DNA of the present invention into an appropriate vector, introducing this into plant cells, and achieving regeneration from the resulting transformed plant cells. A plant's pathogen resistance can be enhanced, for example, by using the AAM 97746.1 gene as the DNA, introducing it into an arbitrary plant variety, and then expressing it. The time required for transformation by this method is much shorter than that required by conventional crossing-based gene transfer. This method is also more advantageous than other methods since it does not cause changes in other traits.

The type of vector to be used in the plant cell transformations is not limited, as long as it can express inserted genes in the cells. For example, it is possible to use a vector comprising a promotor for constitutive gene expression in plant cells (for example, the 35S promoter of cauliflower mosaic virus), or a vector comprising a promoter that is activated upon induction by an exogenous stimulation. The vectors of the present invention are preferably vectors comprising promoters that are activated upon induction by an exogenous stimulation, and more preferably vectors that are inducebly activated against the invasion of pathogens such as pathogenic microorganisms and pests.

Introduction of the vectors into plant cells is achieved by methods known to those skilled in the art, such as polyethylene glycol methods, electroporation, *Agrobacterium*-mediated methods, and particle gun methods.

Plants can be regenerated from transformed plant cells by methods suited to the type of plant cells that are known to those skilled in the art (see Toki et al. (1995) Plant Physiol. 100:1503-1507).

For example, methods known to those skilled in the art for preparing transformant rice plants include methods in which a gene is introduced into a protoplast by polyethylene glycol, and plants are then regenerated (these methods preferably use Indian rice varieties) (Datta, S. K. (11995) In Gene Transfer To Plants (Potrykus I and Spangenberg Eds.) pp66-74), methods in which a gene is introduced into a protoplast by electric pulses and plants are then regenerated (these methods preferably use Japanese rice varieties) (Toki et al. (1992) Plant Physiol. 100, 1503-1507), methods in which a gene is introduced directly into cells by a particle gun method and plants are then regenerated (Christou et al. (1991) Bio/technology, 9: 957-962.), and methods in which a gene is introduced via *Agrobacterium* and plants are then regenerated (Hiei et al. (1994) Plant J. 6: 271-282.). The plant transformants of the present invention can be prepared by these methods. Methods in which a gene is introduced via *Agrobacterium* and plants are then regenerated are preferably used.

Progenies of the plant transformants of the present invention can be obtained via sexual or asexual reproduction from the plant transformants of the present invention, created by the methods described above. Alternatively, breeding materials (for example, seeds, fruits, cut panicles, tubers, tuberous roots, stumps, calluses, and protoplasts) of the transformant plants of the present invention can be obtained from the plants, or progenies or clones thereof, using methods known to those skilled in the art. Thus-obtained progenies and breeding materials can be used to produce the plant transformants of the present invention on a large scale.

(III) Methods for Evaluating the Function of Enhancing Pathogen Resistance

Any method known to those skilled in the art may be used to test whether a protein has the function of enhancing plant resistance to pathogens or not. A plant can be tested, for example, by introducing it with a gene encoding a protein such that the gene is inserted downstream of a viral enhancer region, and then examining whether the plant forms spotted leaves. Specifically, when introducing a plant with a gene that encodes a particular protein causes spotted leaves to form, the protein can be judged to have the function of enhancing plant resistance to pathogens.

Alternative methods for confirming whether a protein has such a function include methods that involve determining the expression level of a PR protein known to be involved in general disease resistance. Specifically, the level of PR protein expression is compared between plant cells (or plants) into which a gene encoding the protein of interest has been introduced, and plant cells (or plants) into which the gene has not been introduced. When the expression level is greater in the plant cells (or plants) into which the gene has been introduced, the protein can be judged to have the function of enhancing plant resistance to pathogens.

The screening methods of the present invention may be any method, as long as it is known to those skilled in the art. For example, the expression of a gene can be found to be enhanced or suppressed by a DNA of the present invention, by determining the expression levels of mRNAs or proteins in cells introduced with the DNA of the present invention and cells into which the DNA has not been introduced, or in cells to which a protein of the present invention has been added and cells to which the protein has not been added, and comparing these levels as described above.

For example, assessment methods based on the expression level of mRNA include differential cloning method (Lau, L. F. and Nathans, D. EMBO J.(1985) 4, 3145-3151), differential display method (Liang, P. and Pardee, A. B. Science (1992) 257, 967-971; Gozo Tsujimoto et al., "Protocols for Genome Function Study (GENOME KINOU KENKYU PROTOCOL)" 1st Ed., Yodosha, Apr. 10, 2000, P. 84-98; Yoshihide Tsujimoto et al., "New edition: Experimental Methods for Apoptosis (SHIN APOPTOSIS JIKKEN-HO)", 2nd Revised Ed., Yodosha, Aug. 10, 1999, p. 289-294), subtractive cloning method (Nucleic Acids Research (1988) 16, 10937), and serial analysis of gene expression (SAGE) method (Velculescu, V. E. et al. Science (1995) 270, 484-487).

Methods of expression analysis that use DNA chips can also be used. For example, whether the expression of a particular gene is altered by a DNA of the present invention or not can be assessed by using different fluorescent dyes to label the cDNAs obtained from cells into which the DNA of the present invention has been introduced and the cDNAs obtained from cells into which the DNA has not been introduced, reacting a DNA chip with a mixture of the cDNAs, and determining the intensity of each dye's fluorescence (Yoshiyuki Sakaki, et al., "New Challenge in Genome Science (GENOME SCIENCE NO ARATANARU CHOSEN)" KYORITSU SHUPPAN CO., LTD. Dec. 20, 2001, p. 2626-2629).

(IV) Methods of Screening for Compounds that Bind to a Protein of the Present Invention These screening methods of the present invention comprise the following steps:

(i) contacting a test compound with a protein of the present invention;

(ii) detecting binding between the test compound and the protein of the present invention; and (iii) selecting compounds which bind to the protein of the present invention.

In the above description, the "test compound" is not limited to a particular compound and can include, for example, single compounds such as natural compounds, organic compounds, inorganic compounds, proteins, and peptides; and libraries of chemical compounds, expression products of gene libraries, cell extracts, cell culture supernatants, products of fermenting microorganisms, extracts of marine organisms, plant extracts, prokaryotic cell extracts, eukaryotic cell extracts, and animal cell extracts. The test compounds described above can be used after labeling appropriately, as required. Such labels include, for example, radioisotope labels and fluorescent labels.

In the above description, contact can be achieved by any method known to those skilled in the art, as long as the method is carried out under conditions where contact between a test compound and a protein of the present invention is possible. Preferably, such contact is suited to the state of protein of the present invention. For example, when the protein of the present invention is in a purified state, contact can be achieved by adding the test compound to the purified sample. Alternatively, when the protein is expressed in cells or cell extracts, contact can be achieved by adding the test compound to the cell culture medium or cell extract. When the test compound is a protein, contact can be achieved, for example, by introducing a vector comprising a DNA encoding the protein into cells expressing a protein of the present invention.

Binding between a test compound and a protein of the present invention may be detected by any method known to those skilled in the art, as long as it is a method for detecting a compound bound to a protein. Binding can be detected, for example, by the following procedure: a test compound is labeled; the compound is allowed to bind to a protein of the present invention according to a method described above; then, the protein of the present invention is separated, purified, and then detected using the label linked to the test compound which is bound to the protein of the present invention (for example, a label enabling a quantitative assay, such as a radioisotope or fluorescent label).

Target compounds of the present invention can be obtained by selecting those compounds judged to bind to a protein of the present invention from the compounds detected by the above procedure.

(V) Methods of Screening for Compounds which Increase the Expression Level of a Gene of the Present Invention These screening methods comprise the following steps of:
(i) providing a cell or cell extract, which comprises a DNA in which a reporter gene has been operably linked downstream of a promoter region of a gene encoding the protein;
(ii) contacting a test compound with the cell or cell extract;
(iii) determining the expression level of the reporter gene in the cell or cell extract; and
(iv) selecting a compound that increases the expression level of the reporter gene as compared with a case where a compound has not been added.

In the above description, the phrase "operably linked" means that a reporter gene is linked to a promoter region of a gene encoding a protein of the present invention, so that the expression of the reporter gene is induced when transcription factors bind to the promoter region of the gene encoding the protein of the present invention. Thus, "operably linked with" also includes cases where the reporter gene is linked to another gene and a fusion protein with the other gene product is produced, as long as expression of that fusion protein is induced when transcription factors bind to the promoter region of the gene encoding the protein of the present invention.

The reporter genes described above are not limited to particular genes, and any gene can be used as long as its expression can be detected. Such reporter genes include, for example, genes generally used by those skilled in the art, such as CAT gene, lacZ gene, luciferase gene, Beta-glucuronidase (GUS), and GFP gene. The reporter genes described above also include DNAs encoding a protein of the present invention.

Cells or cell extracts containing DNAs in which a reporter gene has been operably linked downstream of a promoter region of a gene encoding a protein of the present invention can be prepared by methods known to those skilled in the art.

Contact can be achieved by any method known to those skilled in the art, as long as the method is carried out under conditions where contact between the test compound and the cells containing a reporter gene of the present invention is possible. For example, when the reporter gene is expressed in cells, contact can be achieved by adding a test compound to the cell culture medium. Alternatively, when the reporter gene is expressed in a cell extract, contact can be achieved by adding the test compound to the cell extract. When the test compound is a protein, contact can be achieved, for example, by introducing a vector comprising a DNA encoding the protein into cells that express a protein of the present invention.

The expression level of a reporter gene can be determined by a method known to those skilled in the art, according to the type of reporter gene. For example, when the reporter gene is CAT gene, reporter gene expression level can be determined by detecting chloramphenicol acetylation by the gene product. When the reporter gene is lacZ gene, the reporter gene expression level can be determined by detecting the color development of a dye compound resulting from catalytic activity by the gene expression product. Alternatively, when the reporter gene is luciferase gene, reporter gene expression level can be determined by detecting the fluorescence of the fluorescent compound resulting from the catalytic activity of the gene expression product. When the reporter gene is Beta-glucuronidase gene (GUS), reporter gene expression level can be determined by detecting the luminescence of Glucuron (ICN) or the color development of 5-bromo-4-chloro-3-indolyl-$\beta$-glucuronide (X-Gluc) resulting from the catalytic activity of the gene expression product. When the reporter gene is GFP gene, reporter gene expression level can be determined by detecting the fluorescence of GFP protein.

Alternatively, when a gene encoding a protein of the present invention is used as a reporter, the expression level of the gene can be determined by methods known to those skilled in the art. The transcriptional level of the gene can be determined, for example, by extracting the mRNA of the gene according to a conventional method, and carrying out Northern hybridization or RT-PCR using the mRNA as a template. Alternatively, the expression level of the gene can also be determined using DNA array technology.

The expression level of the gene can also be determined at the translational level by collecting a fraction containing the protein of the present invention encoded by the gene according to a conventional method and detecting expression of the protein of the present invention by electrophoresis, such as SDS-PAGE. Alternatively, the level of gene translation can also be determined by detecting the expression of a protein of the present invention by Western blotting using an antibody against the protein of the present invention. The antibodies used to detect the proteins are not limited to any particular antibody, as long as the detection is possible. For example, both monoclonal and polyclonal antibodies can be used as the antibodies. The antibodies can be prepared by methods known to those skilled in the art.

The target compounds of the methods of the present invention can be obtained by selecting compounds judged to increase the expression level of a gene of the present invention from compounds detected according to the procedures described above.

BRIEF DESCRIPTION OF THE DRAWINGS

FIG. 2 is a diagram showing an example of the nucleotide sequence of the AAM97746.1 gene (SEQ ID NO: 1).

FIG. 3 is a diagram showing the amino acid sequence of the AAM97746.1 protein (SEQ ID NO:2).

BEST MODE FOR CARRYING OUT THE INVENTION

Herein below, the present invention will be specifically described using Examples, however, it is not to be construed as being limited thereto.

EXAMPLE 1

Identification of Proteins Inducing Spotted Leaf

Figure 1:
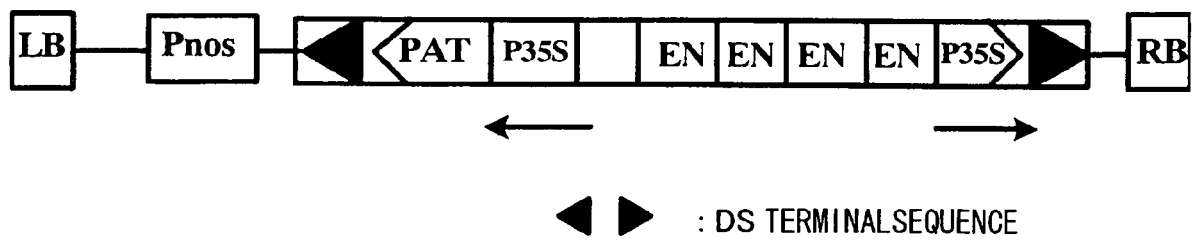
FIG. 1 is a schematic diagram of the activation-tagging vector.

Four copies of an enhancer region (EN) derived from the 35S promoter of cauliflower mosaic virus were ligated in tandem upstream of the core region of the 35S promoter, and the ligate was inserted into T-DNA. Activation-tagging lines were prepared by introducing the activation-tagging vector shown in FIG. 1 into rice (Nipponbare) using the *Agrobacterium* method (seed method). 8,000 subject lines introduced with the gene were obtained using, as an indicator, resistance to 5 μg/ml of bialaphos conferred by the activity of the drug-selection marker PAT.

A single line exhibiting spotted leaves was obtained from subjects into which the gene had been introduced. Genomic DNA was extracted from the first generation transformant of this mutant, and analyzed by Southern blotting. The results showed that a single copy of T-DNA had been inserted (FIG. 4*a*). Analysis of the 29 next-generation subjects yielded 21 subjects exhibiting spotted leaves (FIG. 4*c*). The T-DNA insertion was found in all subjects exhibiting spotted leaves. This result strongly suggests the possibility that the T-DNA insertion caused spotted leaves to develop.

Next, the genome region adjacent to the T-DNA on its RB side was cloned by TAIL-PCR, and its nucleotide sequence was determined (FIG. 2). Then, existence of a putative protein (AAM97746.1; putative acetyl transferase protein) was confirmed 482 bp downstream of the region of the T-DNA insertion (FIG. 3).

EXAMPLE 2

Measurement of the Hypersensitive Reaction Activity of AAM97746.1

Total RNA was extracted from the 29 second-generation subjects obtained in Example 1, and this was analyzed by Northern blotting. The results showed that spotted leaves were found in all plants expressing AAM97746.1, and there was a positive correlation between expression intensity and lesion (spot) severity (FIGS. 4*c* and *d*). Thus, overexpression of AAM97746.1 was found to induce lesion development.

Figure 5:
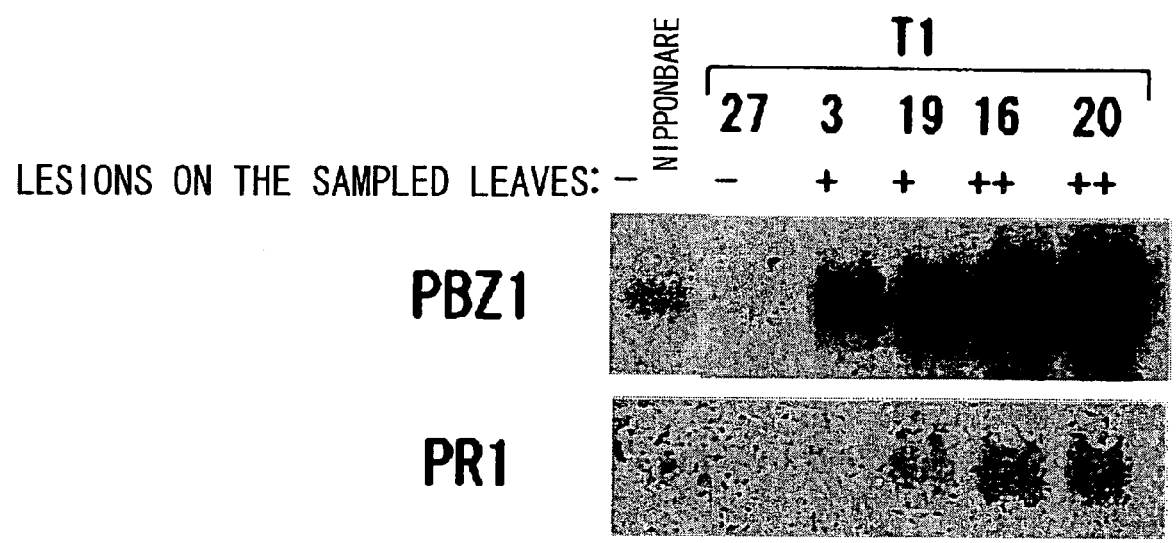
FIG. 5 is a photograph showing the transcriptional activity of PR protein in five second-generation individuals exhibiting spotted leaves.

In addition, Northern blot analysis was used to examine changes in the expression of pathogen related (PR) protein gene in plants exhibiting spotted leaves (FIG. 5). The expression level of PR protein gene was found to be higher in leaves with more severe lesions.

EXAMPLE 3

Test for Blast Resistance

The mutant showing spotted leaves (leaves having lesion-mimic spots) obtained in Example 1 is hereinafter designated as Lmm1 (Lesion mimic 1). The Example 2 results, obtained by measuring hypersensitive reaction activity, showed that expression of the gene associated with disease resistance was increased in Lmm1 (FIG. 5). Thus, resistance was confirmed by inoculating blast fungus to the mutant.

The plants used were six WT (wild type) individuals and six next-generation Lmm1 mutant individuals (subjects unambiguously showing lesion-mimic spots), at the stage of the sixth leaf's development (about 40 days after seeding). The blast fungus used was Kyu89-246 (MAFF101506), race 003.0. The blast fungus was cultured at 25° C. for twelve days in oatmeal medium (Hayashi, N. et al. (1997) Ann. Phytopathol. Soc. Jpn 63: 316-323). Sporulation was allowed under fluorescent lighting for three days. 3 ml of the fungus was inoculated to the plants by spraying at a density of 10×10000/ml. Six days after inoculation, the number of lesions caused by disease was counted.

Figure 6:
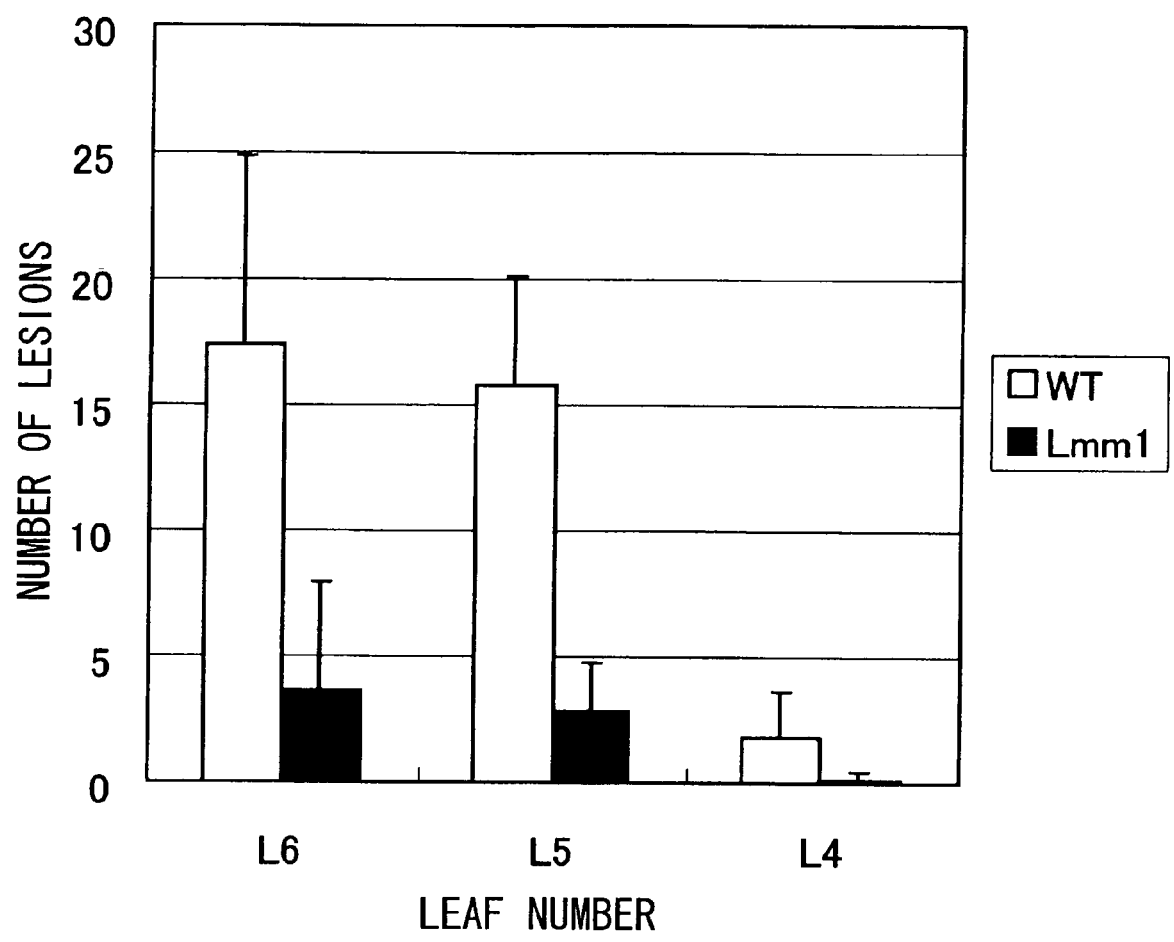
FIG. 6 is a diagram showing the number of lesions (spots) six days after blast fungus inoculation (spraying method).

The results showed that in all tested sixth (L6), fifth (L5), and fourth (L4) leaves of Lmm1, there were fewer disease-caused lesions than in those of WT. Thus Lmm1 was found to exhibit blast resistance (FIG. 6)

EXAMPLE 4

Re-Introduction Experiment

Figure 4:
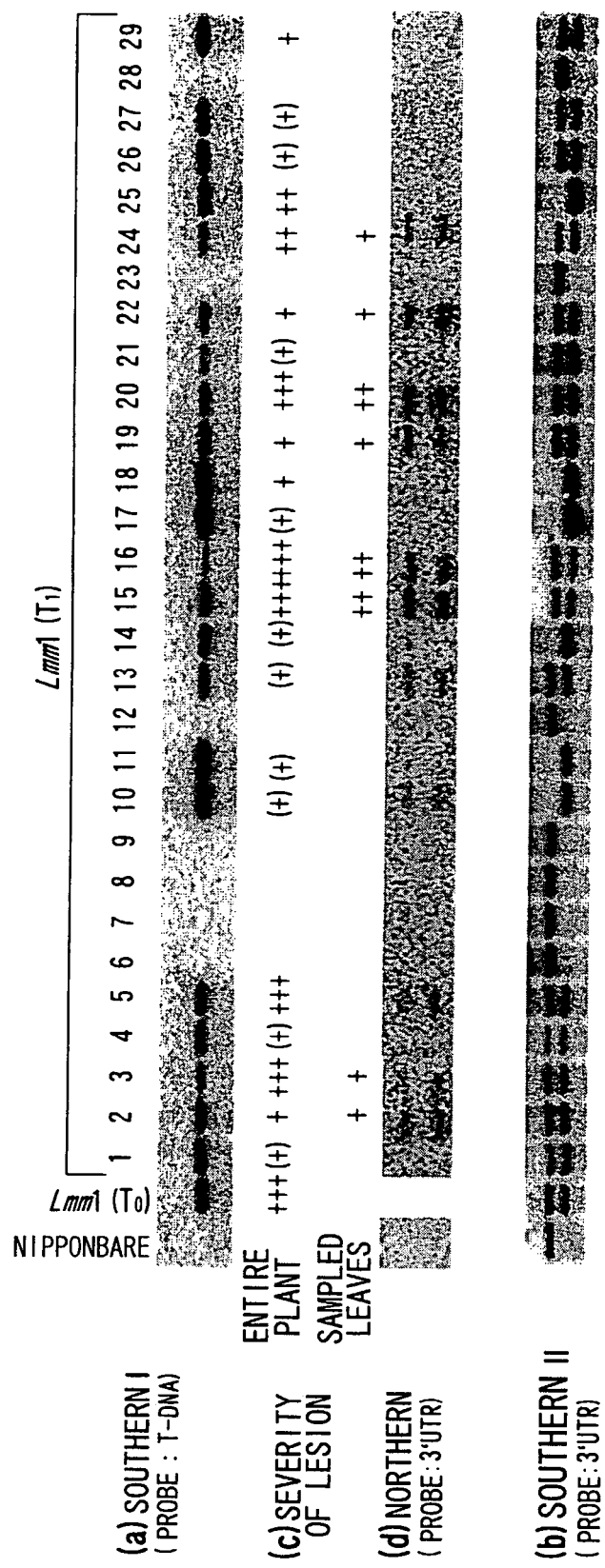
FIG. 4 is photograph and diagram showing confirmation by Southern blot analysis of the presence of T-DNA in the 29 second-generation subjects (FIG. 4a); confirmation of the presence of AAM97746.1 gene (SEQ ID NO: 1) by Southern (FIG. 4b) and Northern blotting (FIG. 4d); and the formation of spotted leaves (FIG. 4c).

The Example 2 results, obtained by measuring hypersensitive reaction activity, showed a positive correlation between the expression level of the gene encoding AAM97746.1 and lesion (lesion-mimic spot) severity (FIG. 4). Thus, the gene encoding AAM97746.1 was ligated to an overexpression vector, and then re-introduced into WT rice to prove that overexpression of the gene is the cause of lesion-mimic spots.

Figure 7:
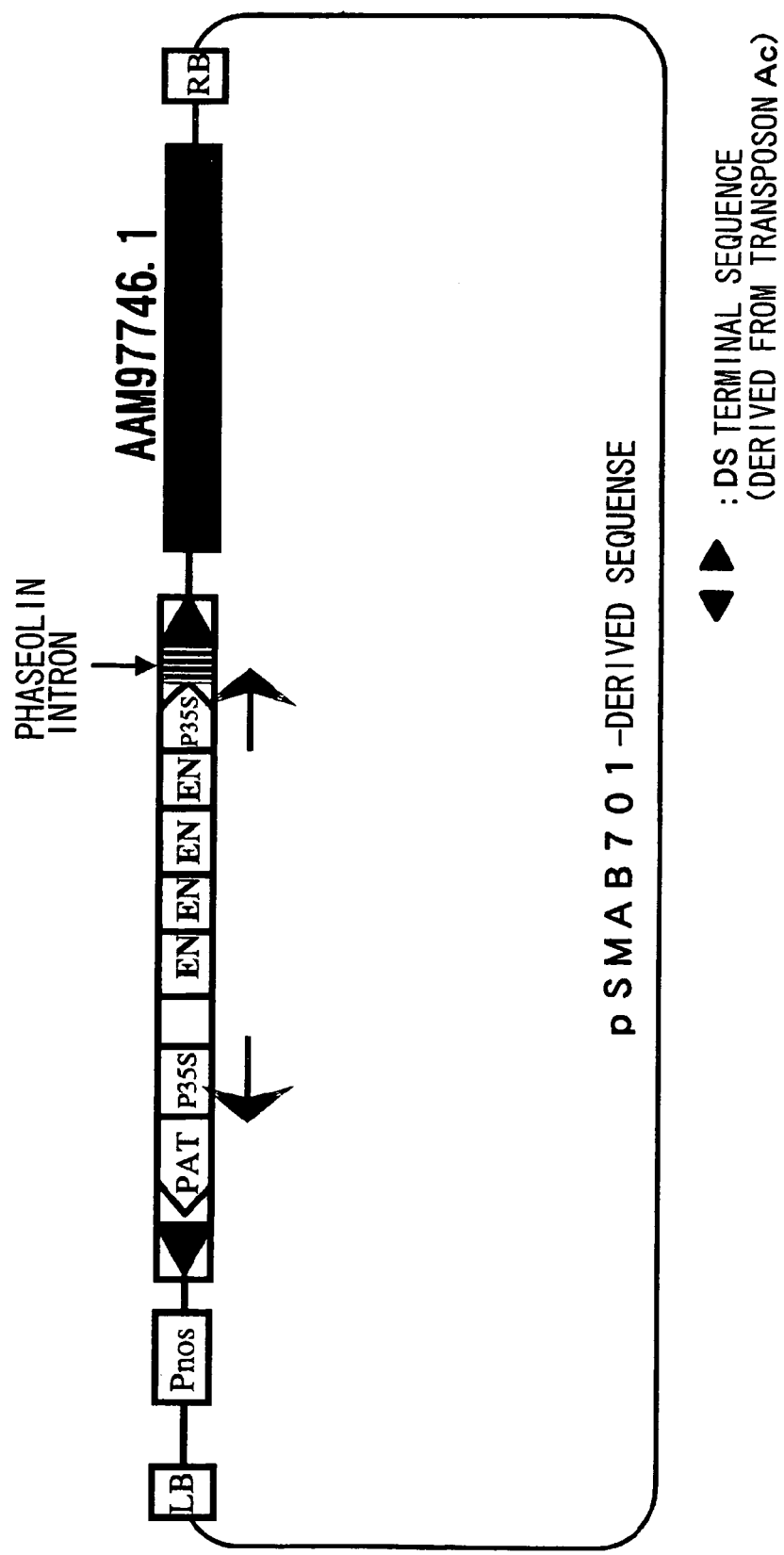
FIG. 7 is a diagram showing the structure of pSMAB-AT1.

The sequence encoding AAM97746.1 shown in FIG. 2 was ligated to an overexpression vector to prepare pSMAB-AT1 (FIG. 7). The resulting vector was introduced into Nipponbare by the same procedure as described in Example 1.

Of the 71 yielded bialaphos-resistant plant individuals, 63 (about 90%) exhibited lesion-mimic spots. This result proves that overexpression of AAM97746.1 is the cause of lesion-mimic spots.

EXAMPLE 5

Test for Resistance to Leaf-Blight Bacteria

The present inventors discovered that transformed rice overexpressing AAM97746.1 protein exhibited resistance to blast disease, a fungal disease. Then, the inventors examined whether rice transformed to overexpress AAM97746.1 protein also exhibited resistance to leaf blight of rice, a bacterial disease.

The rice leaf blight bacterium used was *Xanthomonas oryzae* pv. *oryzae*, Japanese race 1 (T7174). The inoculation was carried out using the clipping method (Kauffman, H. E., Reddy, A. P. K., Hsieh, S. P. Y., and Merca, S. D. 1973. An Improved technique for evaluating resistance of rice varieties to *Xanthomonas oryzae*. Plant Dis. Rep. 57:537-541). Specifically, pairs of scissors were soaked in a $10^8$ cfu/ml bacterial suspension, and then used to clip opened leaves of the transformed rice overexpressing AAM97746.1 protein and control rice (Nipponbare) near the leaf tip. The lengths of lesions in the overexpressing rice plant and the Nipponbare were determined and compared two weeks after inoculation.

Figure 8:
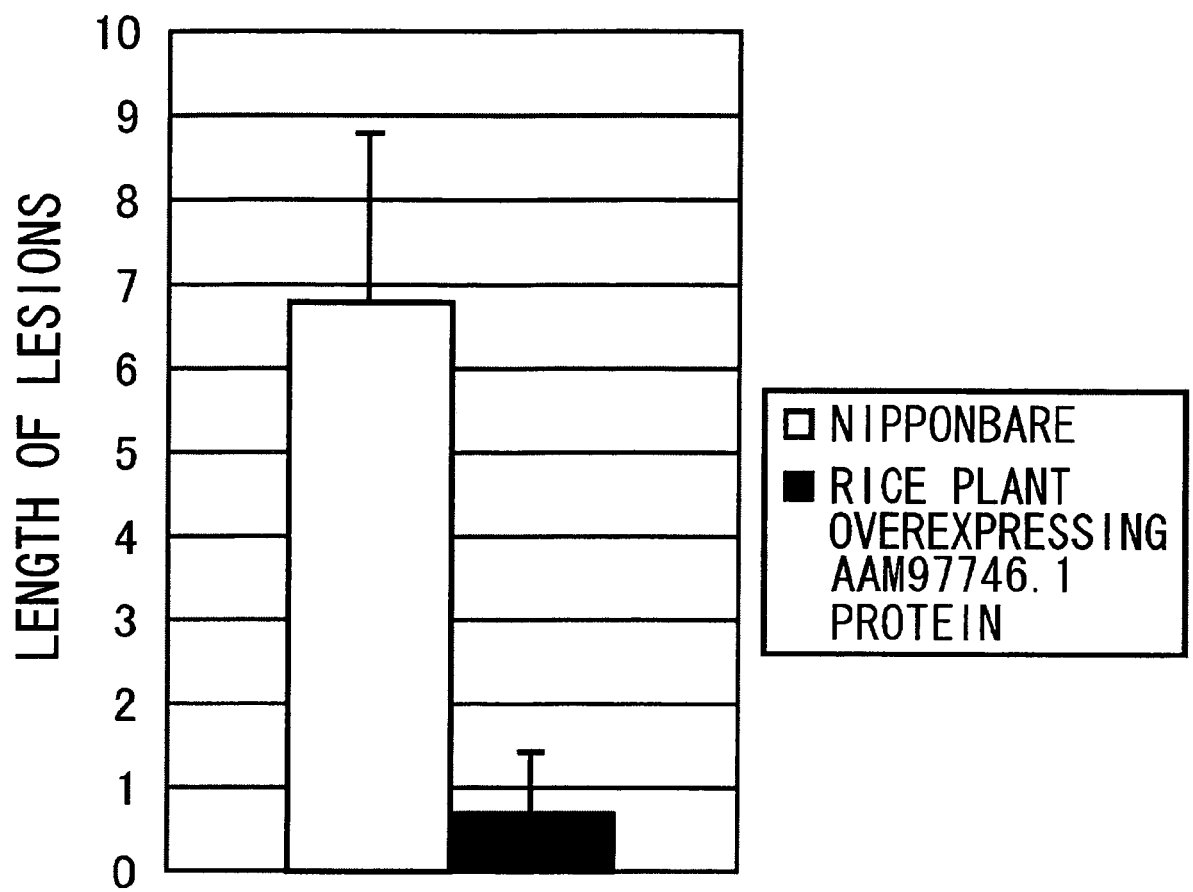
FIG. 8 is a diagram showing the length of lesions after inoculation with leaf-blight bacteria. Length was determined two weeks after inoculation.

The results showed that the mean lesion length was 0.68 cm in the overexpressing rice plant, while in Nipponbare the length was 6.8 cm (FIG. 8). This suggests that the overexpressing rice plant exhibits resistance not only to blast disease, but also to leaf blight. Thus, AAM97746.1 protein can be judged to contribute to resistance to a broad range of diseases in addition to blast disease.

INDUSTRIAL APPLICABILITY

Plant resistance to pathogens is enhanced through hypersensitive reaction, which is induced by the proteins encoded by the DNAs provided by the present invention. Thus, the agents, plant cells, and such of the present invention can enhance the disease and pest resistance of plants, and are useful in breeding pathogen-resistant plants. Furthermore, breeding plant varieties using the genes of the present invention is more advantageous than conventional methods since it can produce desired plants in a short period and with high certainty.

The invention claimed is:

1. A transformed plant cell with enhanced resistance to blast fungus and/or leaf-blight bacteria, comprising an isolated DNA encoding a protein that enhances plant resistance to blast fungus and/or leaf-blight bacteria, wherein the DNA is selected from the group consisting of:
   a) a DNA encoding a protein comprising the amino acid sequence of SEQ ID NO:2; and
   b) a DNA encoding a protein comprising an amino acid sequence having at least 95% identity to the amino acid sequence of SEQ ID NO: 2.

2. The plant cell of claim 1, wherein said DNA is contained within a vector.

3. A transformed plant with enhanced resistance to blast fungus and/or leaf blight bacteria, wherein said transformed plant comprises the plant cell of claim 1.

4. A progeny of the transformed plant of claim 3 with enhanced resistance to blast fungus and/or leaf-blight bacteria, wherein said progeny comprises the isolated DNA.

5. A seed of the transformed plant of claim 3, wherein the seed comprises the isolated DNA.

6. A method of producing a transformed plant cell, the method comprising introducing into the plant cell an isolated DNA encoding a protein that enhances plant resistance to blast fungus and/or leaf-blight bacteria, wherein the DNA is selected from the group consisting of:
   a) a DNA encoding a protein comprising the amino acid sequence of SEQ ID NO:2; and
   b) a DNA encoding a protein comprising an amino acid sequence having at least 95% identity to the amino acid sequence of SEQ ID NO: 2.

7. A transformed plant with enhanced resistance to blast fungus and/or leaf-blight bacteria, wherein said transformed plant comprises the plant cell of claim 2.

8. The method of claim 6, further comprising regenerating a plant from said plant cell.

9. A transformed plant with enhanced resistance to blast fungus and/or leaf-blight bacteria produced by the method of claim 8.

10. A transformed seed from the plant of claim 4.

11. A transformed seed from the plant of claim 7.

12. A transformed seed from the plant of claim 9.

13. A method for producing a transformed plant having enhanced disease resistance, which comprises the steps of:
   a) introducing into a plant cell an isolated DNA encoding a protein that enhances plant resistance to blast fungus and/or leaf-blight bacteria, wherein the DNA is selected from the group consisting of:
      i) a DNA encoding a protein comprising the amino acid sequence of SEQ ID NO:2; and
      ii) a DNA encoding a protein comprising an amino acid sequence having at least 95% identity to the amino acid sequence of SEQ ID NO:2 ; and
   b) regenerating a plant from said plant cell.

* * * * *

SEQUENCE LISTING

```
<160> NUMBER OF SEQ ID NOS: 21

<210> SEQ ID NO 1
<211> LENGTH: 3606
<212> TYPE: DNA
<213> ORGANISM: Oryza sativa
<220> FEATURE:
<221> NAME/KEY: CDS
<222> LOCATION: (482)..(946)
<223> OTHER INFORMATION:
<220> FEATURE:
<221> NAME/KEY: Intron
<222> LOCATION: (947)..(2214)
<223> OTHER INFORMATION:
<220> FEATURE:
<221> NAME/KEY: CDS
<222> LOCATION: (2215)..(3207)
<223> OTHER INFORMATION:

<400> SEQUENCE: 1
agagtttgtt aaagtgggcg tgctatacgg attcaagcaa taactccaca gctatggcca      60
gtacacaagt agttttggc gaagggtaca ttggtcggtt caacttgaca tgggtctttt     120
atctaaatct tatgttaagt agtaaatatt tatgaccaga tagaatatac attttcatga    180
atatgctgta actcatgaat gtccattact tttttggggc cgtgccttta taagtgataa    240
aaatcgtata attagcccta gaaacgactg ccagagtaaa ttctggttaa tggttgaaag    300
catttaatat tctccaagtg ttacttacag gagaaaatta aaccaatgtt aattttcaga    360
tggatataaa accgacgtat ccgtgcgcca ccatcaagca agctcacata tgaaccaccg    420
aagaacatag atagcatcgc ccaacctcgc tgcattcgca ttaccaaagt gtgccaacgc    480 c atg gtg gtg acc ttc aca tct cgc cgg agc gag ccg gtg ctg ctc cgg    529
  Met Val Val Thr Phe Thr Ser Arg Arg Ser Glu Pro Val Leu Leu Arg
    1               5                  10                  15 ccg gcg agg ccg acg ccg cgg gag acg aag cag ctc tcc gac ctc gac    577
Pro Ala Arg Pro Thr Pro Arg Glu Thr Lys Gln Leu Ser Asp Leu Asp
                20                  25                  30 gac cag cgg acg ctg cgg tac tac gag acg gtg gtc ggc ttc ttc cgc    625
Asp Gln Arg Thr Leu Arg Tyr Tyr Glu Thr Val Val Gly Phe Phe Arg
            35                  40                  45 cga tgc gac ggc ggc gca gct ggc gcc gtt ggc gca ccg gcc gac ccg    673
Arg Cys Asp Gly Gly Ala Ala Gly Ala Val Gly Ala Pro Ala Asp Pro
        50                  55                  60 gcc aag gcc atc agg gcg gcg ctc gcg gag gcg ctg gtg tac tac tac    721
Ala Lys Ala Ile Arg Ala Ala Leu Ala Glu Ala Leu Val Tyr Tyr Tyr
65                  70                  75                  80 ccc gtc gcc ggc cgg ctg agg gag gtc gcc gac ggc ggc ggc gcg ggg    769
Pro Val Ala Gly Arg Leu Arg Glu Val Ala Asp Gly Gly Gly Ala Gly
                85                  90                  95 aac cgg ctg gtg gtg gac tgc acg gcc gaa ggg gtg gtg ttc gtg gag    817
Asn Arg Leu Val Val Asp Cys Thr Ala Glu Gly Val Val Phe Val Glu
                100                 105                 110 gcc gac gcc gac gtg cgg ctg gag gac ttc ggc cag ccg ctg ctg ccg    865
Ala Asp Ala Asp Val Arg Leu Glu Asp Phe Gly Gln Pro Leu Leu Pro
            115                 120                 125 ccg tac ccg tgc gtc ggc gag ctg ctc tgc gac gcc ggc gac acc agg    913
Pro Tyr Pro Cys Val Gly Glu Leu Leu Cys Asp Ala Gly Asp Thr Arg
```

```
                 130                 135                 140
gct gtc gtt ggc aaa cca ttg ctc ctc atg cag gtaacaccca cgacgacgta    966
Ala Val Val Gly Lys Pro Leu Leu Leu Met Gln
145                 150                 155 cgtttgtttc tttcattttt gtttacaatc caccactcag ttaatgttta actaacctgt   1026
ctactatata tccgtcctaa gatataacca actaaataaa acatatttta atattacaga   1086
tctgaactgt ggtatattta aatttatatt tattgtgatg tctctaatcc agtattatat   1146
cgctatattt tatggtggag gggtagctaa atactttatt tgtgttttag tgacatgatt   1206
aatttacagt ccatcttatt taccctatgg attggttgta ggcatggatc aagattcatt   1266
cattcgacaa caatattact ttggttgggt ttaggttcac tggtactagg gaccgtgatc   1326
ttaataagga ttcgtaagga cgccacattg ttacgagaac agtgatggta gcttcgtgca   1386
tggttggtag ggattgtacc tactattaat tacagcaacc cactgatctt catttacgca   1446
agaaataatc caactttaga tttgcagatt tgattatgca caaattagtt ctggagttaa   1506
caaatctctt ttctgtgcaa ttggttttat agttttcagt tgccaaactg cttttctttt   1566
gaacactgcc acaaacatga gaaatacaat gaatgtggca tcatattttg ataacaaaaa   1626
cttaaaatac aaatacaaca gccacattaa ctaagattta gtctgaagta gtggtgaatg   1686
ggattggacc agaaaagcat tgaaatggtt attcaacaca acgattagtt ggactggctt   1746
tgggcccatc aagaggggtt ccaactggag tgtgatgttg cagttggatg atatatatat   1806
gggccggcaa tattaagatt gcgaattaag aatgtggtaa tgttgtgttg tattatttc    1866 aatattataa aacgttttag cttctccatc cctcatttaa attcactagc atccatatga   1926
atttgtacag atatataaac acatatacat atgggatcaa gttgcatggt ccgactatat   1986
attcatacta acataaaagg tcggattttc acataatact gacaatactc gagcacggaa   2046
gaattctttt aatgttttat aagaatatat actgcctctg tttcttattt ctgattgagc   2106
tgaccaatgt catatagaag tgtttaggat ggaggtacca tacttaccat gtctaattaa   2166
ttaattaatt tgactgttac tgatttctat atgtggcggt ttcattag gtg acg caa    2223
                                                     Val Thr Gln ctt aaa tgc ggc gga ttc gtc ctg ggc ttc cac atc tgt cac aac atc    2271
Leu Lys Cys Gly Gly Phe Val Leu Gly Phe His Ile Cys His Asn Ile
    160                 165                 170 gct gac ggc ttc ggc atg gcg cag ctg atc atg gcc ata gcc gac ctc    2319
Ala Asp Gly Phe Gly Met Ala Gln Leu Ile Met Ala Ile Ala Asp Leu
175                 180                 185                 190 gca cgt ggt gag cca gcc ccg acc att ctg ccc gta tgg agg agg gac    2367
Ala Arg Gly Glu Pro Ala Pro Thr Ile Leu Pro Val Trp Arg Arg Asp
                195                 200                 205 cta ctc acg gca gca cgc cta ggt agc ggc gcg gtg gca cgc acg ccc    2415
Leu Leu Thr Ala Ala Arg Leu Gly Ser Gly Ala Val Ala Arg Thr Pro
            210                 215                 220 ttt gca tcg gcg gcg gcg gcg tcg gcc tcg gcg tcg agc ccg gca cta    2463
Phe Ala Ser Ala Ala Ala Ala Ser Ala Ser Ala Ser Ser Pro Ala Leu
        225                 230                 235 cag aac ggt gct cgc cgc gcc gcc gcc gcg gct gac gcg atg ctg tcg    2511
Gln Asn Gly Ala Arg Arg Ala Ala Ala Ala Ala Asp Ala Met Leu Ser
    240                 245                 250 acc ccg ccg gac cgg atg gtg gtg gag tac ttc ctg ttc ggg cca cgg    2559
Thr Pro Pro Asp Arg Met Val Val Glu Tyr Phe Leu Phe Gly Pro Arg
255                 260                 265                 270 gag gtg tcc tac ctg cgt ggc cag ctg ccg gcg cac ctg gcg gac tcc    2607
Glu Val Ser Tyr Leu Arg Gly Gln Leu Pro Ala His Leu Ala Asp Ser
```

-continued

| | | | |
|---|---|---|---|
| | 275 | 280 | 285 |

| | | |
|---|---|---|
| acc acg gtg ttc gag ctg ctc acc gcc gtc atg tgg cgg tgc cgc acg<br>Thr Thr Val Phe Glu Leu Leu Thr Ala Val Met Trp Arg Cys Arg Thr<br>                290                           295                             300 | 2655 |
| gcg gcg ctc ggg tac ggg ccc gac ctc cgc gtc cgg cta atg atc acc<br>Ala Ala Leu Gly Tyr Gly Pro Asp Leu Arg Val Arg Leu Met Ile Thr<br>305                            310                           315 | 2703 |
| atg aac gcg cgc ggg agg tgg aac gcg cac acc ccg ctc ccg cgc ggc<br>Met Asn Ala Arg Gly Arg Trp Asn Ala His Thr Pro Leu Pro Arg Gly<br>    320                          325                           330 | 2751 |
| ttc tac ggc aac gcg cac gtc tcc ccc gtc gcc gag gcc gcc gcc ggc<br>Phe Tyr Gly Asn Ala His Val Ser Pro Val Ala Glu Ala Ala Ala Gly<br>335                            340                          345                           350 | 2799 |
| gac ctc ctc ggg cgg ccg ctc gcc gac acg gtg gag ctc gtg cgg agg<br>Asp Leu Leu Gly Arg Pro Leu Ala Asp Thr Val Glu Leu Val Arg Arg<br>                355                           360                         365 | 2847 |
| acc aag cgc ggg atg acg cgg gag cgg atg agc gcc atg gtg gag acg<br>Thr Lys Arg Gly Met Thr Arg Glu Arg Met Ser Ala Met Val Glu Thr<br>                      370                           375                         380 | 2895 |
| gtg gcg cag ctg cgg gag tgg ccg ccg tcg agc atg gac agg gtg tac<br>Val Ala Gln Leu Arg Glu Trp Pro Pro Ser Ser Met Asp Arg Val Tyr<br>385                            390                           395 | 2943 |
| gag gtc tcc gac atc aag tgg acc acc gtg aac ttg ctc aag ttc ggg<br>Glu Val Ser Asp Ile Lys Trp Thr Thr Val Asn Leu Leu Lys Phe Gly<br>    400                          405                           410 | 2991 |
| tgg gct gag ttc gcc ggc ggc ggc ata ccg ctc gca ggc gat ctc acc<br>Trp Ala Glu Phe Ala Gly Gly Gly Ile Pro Leu Ala Gly Asp Leu Thr<br>415                            420                          425                           430 | 3039 |
| tcc aag ctc gga agc gac cac acg agg tgc aag aac tcg gcc ggc gag<br>Ser Lys Leu Gly Ser Asp His Thr Arg Cys Lys Asn Ser Ala Gly Glu<br>                435                           440                         445 | 3087 |
| gtg tcg acg gtg gtg tcg atg ctg ctg ccc agg gtg gcc atg gcg agg<br>Val Ser Thr Val Val Ser Met Leu Leu Pro Arg Val Ala Met Ala Arg<br>                      450                         455                        460 | 3135 |
| ttc aag aag gag atg gcc gtt ttg ttg aac aaa gat gac aag aag agc<br>Phe Lys Lys Glu Met Ala Val Leu Leu Asn Lys Asp Asp Lys Lys Ser<br>465                            470                         475 | 3183 |
| ttg aca att atg agt tcg ctg tag ttgttgc cacacatttc aagcaaaggt<br>Leu Thr Ile Met Ser Ser Leu<br>    480                  485 | 3234 |
| tcttaaacag ctaatggtca ccaaagcaca ttttttatcac tgtcacttca tcatttctga | 3294 |
| tcgatctagt tgtgcacatc taatttagtg ggacaatcgg tttacttagt ggagtactac | 3354 |
| aatatatgta attgtattca gttgtgtcta cctgttcatc tgcacaggct attggatttt | 3414 |
| catcagttct ttaattgtaa aatacacccc tcccttttaat gtatgcgcac atacttttaa | 3474 |
| cttgtaaagt tacctcgctc attatagttt gtaatgtgag cttttttataa atttgtttct | 3534 |
| attacttatg acggaaaaga taaagaaaa taattaaatt aaactcctct tgtaaccttg | 3594 |
| gagcggccta cg | 3606 |

<210> SEQ ID NO 2
<211> LENGTH: 485
<212> TYPE: PRT
<213> ORGANISM: Oryza sativa

<400> SEQUENCE: 2

Met Val Val Thr Phe Thr Ser Arg Arg Ser Glu Pro Val Leu Leu Arg
1                 5                    10                  15

-continued

```
Pro Ala Arg Pro Thr Pro Arg Glu Thr Lys Gln Leu Ser Asp Leu Asp
         20                  25                  30

Asp Gln Arg Thr Leu Arg Tyr Tyr Glu Thr Val Val Gly Phe Phe Arg
             35                  40                  45

Arg Cys Asp Gly Gly Ala Ala Gly Ala Val Gly Ala Pro Ala Asp Pro
 50                  55                  60

Ala Lys Ala Ile Arg Ala Ala Leu Ala Glu Ala Leu Val Tyr Tyr Tyr
 65                  70                  75                  80

Pro Val Ala Gly Arg Leu Arg Glu Val Ala Asp Gly Gly Ala Gly
             85                  90                  95

Asn Arg Leu Val Val Asp Cys Thr Ala Glu Gly Val Val Phe Val Glu
                100                 105                 110

Ala Asp Ala Asp Val Arg Leu Glu Asp Phe Gly Gln Pro Leu Leu Pro
             115                 120                 125

Pro Tyr Pro Cys Val Gly Glu Leu Leu Cys Asp Ala Gly Asp Thr Arg
         130                 135                 140

Ala Val Val Gly Lys Pro Leu Leu Leu Met Gln Val Thr Gln Leu Lys
145                 150                 155                 160

Cys Gly Gly Phe Val Leu Gly Phe His Ile Cys His Asn Ile Ala Asp
                165                 170                 175

Gly Phe Gly Met Ala Gln Leu Ile Met Ala Ile Ala Asp Leu Ala Arg
             180                 185                 190

Gly Glu Pro Ala Pro Thr Ile Leu Pro Val Trp Arg Arg Asp Leu Leu
         195                 200                 205

Thr Ala Ala Arg Leu Gly Ser Gly Ala Val Ala Arg Thr Pro Phe Ala
210                 215                 220

Ser Ala Ala Ala Ser Ala Ser Ala Ser Ser Pro Ala Leu Gln Asn
225                 230                 235                 240

Gly Ala Arg Arg Ala Ala Ala Ala Asp Ala Met Leu Ser Thr Pro
             245                 250                 255

Pro Asp Arg Met Val Val Glu Tyr Phe Leu Phe Gly Pro Arg Glu Val
         260                 265                 270

Ser Tyr Leu Arg Gly Gln Leu Pro Ala His Leu Ala Asp Ser Thr Thr
             275                 280                 285

Val Phe Glu Leu Leu Thr Ala Val Met Trp Arg Cys Arg Thr Ala Ala
290                 295                 300

Leu Gly Tyr Gly Pro Asp Leu Arg Val Arg Leu Met Ile Thr Met Asn
305                 310                 315                 320

Ala Arg Gly Arg Trp Asn Ala His Thr Pro Leu Pro Arg Gly Phe Tyr
             325                 330                 335

Gly Asn Ala His Val Ser Pro Val Ala Glu Ala Ala Gly Asp Leu
         340                 345                 350

Leu Gly Arg Pro Leu Ala Asp Thr Val Glu Leu Val Arg Arg Thr Lys
             355                 360                 365

Arg Gly Met Thr Arg Glu Arg Met Ser Ala Met Val Glu Thr Val Ala
         370                 375                 380

Gln Leu Arg Glu Trp Pro Ser Ser Met Asp Arg Val Tyr Glu Val
385                 390                 395                 400

Ser Asp Ile Lys Trp Thr Thr Val Asn Leu Leu Lys Phe Gly Trp Ala
             405                 410                 415

Glu Phe Ala Gly Gly Gly Ile Pro Leu Ala Gly Asp Leu Thr Ser Lys
         420                 425                 430

Leu Gly Ser Asp His Thr Arg Cys Lys Asn Ser Ala Gly Glu Val Ser
```

```
                435                440                445
            Thr Val Val Ser Met Leu Leu Pro Arg Val Ala Met Ala Arg Phe Lys
                450                455                460

Lys Glu Met Ala Val Leu Leu Asn Lys Asp Asp Lys Lys Ser Leu Thr
            465                470                475                480

Ile Met Ser Ser Leu
                            485

<210> SEQ ID NO 3
<211> LENGTH: 1458
<212> TYPE: DNA
<213> ORGANISM: Oryza sativa

<400> SEQUENCE: 3
atggtggtga ccttcacatc tcgccggagc gagccggtgc tgctccggcc ggcgaggccg       60
acgccgcggg agacgaagca gctctccgac ctcgacgacc agcggacgct gcggtactac      120
gagacggtgg tcggcttctt ccgccgatgc gacgcggcg cagctggcgc cgttggcgca      180
ccggccgacc cggccaaggc catcaggcg cgctcgcgg aggcgctggt gtactactac      240 ccgtcgccg gccggctgag ggaggtcgcc gacgcggcg gcgcggggaa ccggctggtg      300
gtggactgca cggccgaagg ggtggtgttc gtggaggccg acgccgacgt gcggctggag      360
gacttcggcc agccgctgct gccgccgtac ccgtgcgtcg gcgagctgct ctgcgacgcc      420
ggcgacacca gggctgtcgt tggcaaacca ttgctcctca tgcaggtgac gcaacttaaa      480
tgcggcggat tcgtcctggg cttccacatc tgtcacaaca tcgctgacgg cttcggcatg      540
gcgcagctga tcatggccat agccgacctc gcacgtggtg agccagcccc gaccattctg      600
cccgtatgga ggagggacct actcacgca gcacgcctag gtagcggcgc ggtggcacgc      660 acgcccttt catcggcggc ggcggcgtcg gcctcggcgt cgagcccggc actacagaac      720
ggtgctcgcc gcgccgccgc gcggctgac gcgatgctgt cgaccccgcc ggaccggatg      780
gtggtggagt acttcctgtt cgggccacgg gaggtgtcct acctgcgtgg ccagctgccg      840
gcgcacctgg cggactccac cacggtgttc gagctgctca ccgccgtcat gtggcggtgc      900
cgcacggcgg cgctcgggta cgggcccgac ctccgcgtcc ggctaatgat caccatgaac      960
gcgcgcggga ggtggaacgc gcacaccccg ctcccgcgcg gcttctacgg caacgcgcac     1020
gtctcccccg tcgccgaggc cgccgccggc gacctcctcg gcggccgct cgccgacacg     1080 gtggagctcg tgcggaggac caagcgcggg atgacgcggg agcggatgag cgccatggtg     1140
gagacggtgg cgcagctgcg ggagtggccg ccgtcgagca tggacagggt gtacgaggtc     1200
tccgacatca gtggaccac cgtgaacttg ctcaagttcg ggtgggctga gttcgccggc     1260
ggcggcatac cgctcgcagg cgatctcacc tccaagctcg gaagcgacca cacgaggtgc     1320
aagaactcgg ccggcgaggt gtcgacggtg gtgtcgatgc tgctgcccag ggtggccatg     1380
gcgaggttca agaaggagat ggccgttttg ttgaacaaag atgacaagaa gagcttgaca     1440
attatgagtt cgctgtag                                                   1458

<210> SEQ ID NO 4
<211> LENGTH: 3000
<212> TYPE: DNA
<213> ORGANISM: Oryza sativa
<220> FEATURE:
<221> NAME/KEY: CDS
<222> LOCATION: (507)..(962)
<223> OTHER INFORMATION:
<220> FEATURE:
```

-continued

```
<221> NAME/KEY: Intron
<222> LOCATION: (963)..(1631)
<223> OTHER INFORMATION:
<220> FEATURE:
<221> NAME/KEY: CDS
<222> LOCATION: (1632)..(2585)
<223> OTHER INFORMATION:

<400> SEQUENCE: 4
```

| | |
|---|---|
| gttgtccaaa ttggtttgaa ggatgcgtgg gtgattgatc cctggaattg cgctaaatag | 60 |
| ggttaattca gtagagaaga gataacaaat gcaagactta gttcctgact aactgactat | 120 |
| tcagaatttc agatagtcat aacactcatt cagattcaag gccgaggtc caccccatga | 180 |
| gctctgcaac ttgactaaaa gggagaaatt tctttggaga cttttgagca gttgacagag | 240 |
| ccctgcatgc cagctgctag cttccaagag atcttccaaa cctttaacat tatagaaaaa | 300 |
| gcaaacacca aaatatatgc ctccacccat ttccaggcgt tcccatgcaa cgttggcaga | 360 |
| aagaaaacgc actatatata ccggctgaag ctccatcact ctgatccatc cactgcaact | 420 |
| gatcaggcaa agaggaattc attatacaaa gctaagctaa gtttcagctt ctcatcagtc | 480 |
| tcccagtttc aggtcggtcg tgcacc atg gtg gcc act ttc acg gca cgc cgg | 533 |
|        Met Val Ala Thr Phe Thr Ala Arg Arg | |
|          1               5 | |
| agc tcg ccg gag ctg gtg acg ccg gct agg ccg acg cca cgt gag acc | 581 |
| Ser Ser Pro Glu Leu Val Thr Pro Ala Arg Pro Thr Pro Arg Glu Thr | |
|  10              15                  20                  25 | |
| aag ctg ctg tcc gac ctc gac gac cag tgg acg ctg cgc tac tac gag | 629 |
| Lys Leu Leu Ser Asp Leu Asp Asp Gln Trp Thr Leu Arg Tyr Tyr Glu | |
|              30                  35                  40 | |
| acc gtc gtg ggg ttc ttc cgc gtc tcc ccc aag atg gcc ggc ggc ctg | 677 |
| Thr Val Val Gly Phe Phe Arg Val Ser Pro Lys Met Ala Gly Gly Leu | |
|          45                  50                  55 | |
| ccc ggc ggc gac aac atc gcc gcc aag gtg atc aag gcg gcc gtc gcc | 725 |
| Pro Gly Gly Asp Asn Ile Ala Ala Lys Val Ile Lys Ala Ala Val Ala | |
|              60                  65                  70 | |
| gag gcc ctc gtg cac tac tac cct gtg gcc ggc cgc ctg cgg gct ctc | 773 |
| Glu Ala Leu Val His Tyr Tyr Pro Val Ala Gly Arg Leu Arg Ala Leu | |
|  75                  80                  85 | |
| gtc ccc ggc ggg aac aag ctg gcc gtg gac tgc acg gcg gaa ggg gtg | 821 |
| Val Pro Gly Gly Asn Lys Leu Ala Val Asp Cys Thr Ala Glu Gly Val | |
|  90                  95                 100                 105 | |
| gcg ttc gtc gag gcc acc gcc gac gtg cgg ctg gag gag ctc ggc gag | 869 |
| Ala Phe Val Glu Ala Thr Ala Asp Val Arg Leu Glu Glu Leu Gly Glu | |
|                 110                 115                 120 | |
| ccg ctg ctg ccg ccg tat ccg tgt gtc gag gag ttc ctc ggt gat gcc | 917 |
| Pro Leu Leu Pro Pro Tyr Pro Cys Val Glu Glu Phe Leu Gly Asp Ala | |
|             125                 130                 135 | |
| ggc gac act agg gat atc cta gac aag cct ctg ctc ttc ctg cag | 962 |
| Gly Asp Thr Arg Asp Ile Leu Asp Lys Pro Leu Leu Phe Leu Gln | |
|             140                 145                 150 | |
| gtatatatat gtctcaattg attagccttt cagatgtttt ctttcaaatt ttaaatttac | 1022 |
| aaccaaggca tctgttacta cctgaccgat tcattaaaat tttacgcgca cggtttgcaa | 1082 |
| tttcgtttct aaatttcggg tcccccatct cccctagcg cgaaactatt ttgcctaatg | 1142 |
| tttctttttt cttttctgaa ttaagaaaaa aaacaccca tttgtttag tattagatgt | 1202 |
| gacataggag tagttagtag tagtattatg aatttggaca aaccccacaa catagcctgt | 1262 |
| tttgctcata gcatagcagt actactccct ctagttttt atatgacgtt agctagttta | 1322 |
| aatttatagt agcccacgtc atatgcacgg aggtagtagc taggttgtgt tccatttagc | 1382 |

-continued

```
actaggatac tatatttgga acggaagtag tattcaaatt ggctcaacgt ttattcaaaa   1442
ttcaaattat tttggatcga aaatattcca aattttcaga aattgtggat ttatcagtcc   1502
ctgaattttt ttttaggcct tccgaaattg tgttagccct gtgttaagcg tacgtacata   1562
tgtttcagat ctgaatgtct aacaatccgt tggttaatcc tatctctgct ttcgaacgaa   1622
tatatgtag gtg act caa ctg aaa tgc ggt gga ttt gtc atc ggc ctc cac   1673
          Val Thr Gln Leu Lys Cys Gly Gly Phe Val Ile Gly Leu His
                  155                 160                 165
atg tgc cac tgc att ttt gac gcc ttc ggc ctg ctc cag ttc atc aaa     1721
Met Cys His Cys Ile Phe Asp Ala Phe Gly Leu Leu Gln Phe Ile Lys
            170                 175                 180
acc ata gct ggt ttc gcc ggc ggt gaa cca atc cca tcc acc atg ccc     1769
Thr Ile Ala Gly Phe Ala Gly Gly Glu Pro Ile Pro Ser Thr Met Pro
        185                 190                 195
gtg tgg ggc aga gag tcg ttc ttc gca gca cgg aca cca cca tcc ttc     1817
Val Trp Gly Arg Glu Ser Phe Phe Ala Ala Arg Thr Pro Pro Ser Phe
    200                 205                 210
acc cat gtc tac ccg gca tac aag ccg atc ctc gac ggc cgg agc agc     1865
Thr His Val Tyr Pro Ala Tyr Lys Pro Ile Leu Asp Gly Arg Ser Ser
215                 220                 225                 230
gca ggc gac ggc gac ggc gac gtc gac gat gtg atg ctg aca act cca     1913
Ala Gly Asp Gly Asp Gly Asp Val Asp Asp Val Met Leu Thr Thr Pro
                235                 240                 245
cct gaa acc atg gtg atg aag tac ttc agc ttc ggg cca aaa gag atc     1961
Pro Glu Thr Met Val Met Lys Tyr Phe Ser Phe Gly Pro Lys Glu Ile
            250                 255                 260
tcg gct ctc cgg agc ctg atc cct gca cac ctc acc aga tcc acc acg     2009
Ser Ala Leu Arg Ser Leu Ile Pro Ala His Leu Thr Arg Ser Thr Thr
        265                 270                 275
gca ttc gag ctg ctc acc gcg gtc atg tgg cga tgc cgc acg tcg gcg     2057
Ala Phe Glu Leu Leu Thr Ala Val Met Trp Arg Cys Arg Thr Ser Ala
    280                 285                 290
ctg ggg tac gag ccc gat cga cgc gtg cgc ctc atg ttc acc ctg aat     2105
Leu Gly Tyr Glu Pro Asp Arg Arg Val Arg Leu Met Phe Thr Leu Asn
295                 300                 305                 310
cta cga ggg aga tgg tgg agc cgc gaa gaa gaa gcc gcc gtg ccg ccg     2153
Leu Arg Gly Arg Trp Trp Ser Arg Glu Glu Glu Ala Ala Val Pro Pro
                315                 320                 325
ggc tac tac ggg aac gcg cat ctc tcc ccc atg gtg acg gcc acc gtc     2201
Gly Tyr Tyr Gly Asn Ala His Leu Ser Pro Met Val Thr Ala Thr Val
            330                 335                 340
ggc gag ctg gcc cgg cag cct ctc gcg gac acc gtc gag ctc atg tgc     2249
Gly Glu Leu Ala Arg Gln Pro Leu Ala Asp Thr Val Glu Leu Met Cys
        345                 350                 355
agg gcc aag gcc ggc acg acg agg gag cgc gtg gag tcg atg gtt gat     2297
Arg Ala Lys Ala Gly Thr Thr Arg Glu Arg Val Glu Ser Met Val Asp
    360                 365                 370
ctc ctg gcg aca tgg cgg gag cgg ccg gcg ttc gcc atg gac agg acg     2345
Leu Leu Ala Thr Trp Arg Glu Arg Pro Ala Phe Ala Met Asp Arg Thr
375                 380                 385                 390
tat gag gtt tct gac acg aaa tgg gtc ggt gga gga ggc ggt gcg ttg     2393
Tyr Glu Val Ser Asp Thr Lys Trp Val Gly Gly Gly Gly Gly Ala Leu
                395                 400                 405
cgc tgt ggg gtg gcg gag atg gtc ggc ggc ggc acg cct ttc gcc gga     2441
Arg Cys Gly Val Ala Glu Met Val Gly Gly Gly Thr Pro Phe Ala Gly
            410                 415                 420
gac ctc acc tcg aag ctg ata agc tat cac atg aaa tgc aag aac gaa     2489
Asp Leu Thr Ser Lys Leu Ile Ser Tyr His Met Lys Cys Lys Asn Glu
```

```
                     425                 430                 435
aat ggg gag gac tcg att gtg gtg tcg atg ttg ttg cca gag cca gcg    2537
Asn Gly Glu Asp Ser Ile Val Val Ser Met Leu Leu Pro Glu Pro Ala
    440                 445                 450 atg gag agg ttc acg aag gag atg tcg ttt tgg ctg aag agc tat taa    2585
Met Glu Arg Phe Thr Lys Glu Met Ser Phe Trp Leu Lys Ser Tyr
455                 460                 465 cggatag atatgtctca gtatgatcct tgggatgtta tatgatggaa caaccttagc     2642
tttcaataag gggatgaaga gttgtttgta tacatatttt gttcttgtat actttcgtta  2702
ctagaaggtt gggagccatc ctagaaataa tcacatatat actacacata gcatgcatgg  2762
ctatgtgtag aactcgtata tatatttcta ataaataaaa atggtattgt tatggttctc  2822
taagttcttt ttaagataaa atgatctatt ttttttctg catcactgca tgggataatg   2882
tcaggagctt gacttggcag catatgggca ggttcagcca ttttcaagcc cagttcataa  2942
aagcccaagg cagtggcgga cacaggattt tgacgatagg tatacgaaat tatgaagt    3000

<210> SEQ ID NO 5
<211> LENGTH: 469
<212> TYPE: PRT
<213> ORGANISM: Oryza sativa

<400> SEQUENCE: 5

Met Val Ala Thr Phe Thr Ala Arg Arg Ser Ser Pro Glu Leu Val Thr
1               5                   10                  15

Pro Ala Arg Pro Thr Pro Arg Glu Thr Lys Leu Leu Ser Asp Leu Asp
            20                  25                  30

Asp Gln Trp Thr Leu Arg Tyr Tyr Glu Thr Val Val Gly Phe Phe Arg
        35                  40                  45

Val Ser Pro Lys Met Ala Gly Leu Pro Gly Gly Asp Asn Ile Ala
    50                  55                  60

Ala Lys Val Ile Lys Ala Val Ala Glu Ala Leu Val His Tyr Tyr
65                  70                  75                  80

Pro Val Ala Gly Arg Leu Arg Ala Leu Val Pro Gly Gly Asn Lys Leu
                85                  90                  95

Ala Val Asp Cys Thr Ala Glu Gly Val Ala Phe Val Glu Ala Thr Ala
            100                 105                 110

Asp Val Arg Leu Glu Glu Leu Gly Glu Pro Leu Leu Pro Pro Tyr Pro
        115                 120                 125

Cys Val Glu Glu Phe Leu Gly Asp Ala Gly Asp Thr Arg Asp Ile Leu
    130                 135                 140

Asp Lys Pro Leu Leu Phe Leu Gln Val Thr Gln Leu Lys Cys Gly Gly
145                 150                 155                 160

Phe Val Ile Gly Leu His Met Cys His Cys Ile Phe Asp Ala Phe Gly
                165                 170                 175

Leu Leu Gln Phe Ile Lys Thr Ile Ala Gly Phe Ala Gly Gly Glu Pro
            180                 185                 190

Ile Pro Ser Thr Met Pro Val Trp Gly Arg Glu Ser Phe Phe Ala Ala
        195                 200                 205

Arg Thr Pro Pro Ser Phe Thr His Val Tyr Pro Ala Tyr Lys Pro Ile
    210                 215                 220

Leu Asp Gly Arg Ser Ser Ala Gly Asp Gly Asp Val Asp Asp
225                 230                 235                 240

Val Met Leu Thr Thr Pro Pro Glu Thr Met Val Met Lys Tyr Phe Ser
                245                 250                 255
```

```
Phe Gly Pro Lys Glu Ile Ser Ala Leu Arg Ser Leu Ile Pro Ala His
            260                 265                 270

Leu Thr Arg Ser Thr Thr Ala Phe Glu Leu Leu Thr Ala Val Met Trp
        275                 280                 285

Arg Cys Arg Thr Ser Ala Leu Gly Tyr Glu Pro Asp Arg Arg Val Arg
        290                 295                 300

Leu Met Phe Thr Leu Asn Leu Arg Gly Arg Trp Trp Ser Arg Glu Glu
305                 310                 315                 320

Glu Ala Ala Val Pro Pro Gly Tyr Tyr Gly Asn Ala His Leu Ser Pro
                325                 330                 335

Met Val Thr Ala Thr Val Gly Glu Leu Ala Arg Gln Pro Leu Ala Asp
            340                 345                 350

Thr Val Glu Leu Met Cys Arg Ala Lys Ala Gly Thr Thr Arg Glu Arg
        355                 360                 365

Val Glu Ser Met Val Asp Leu Leu Ala Thr Trp Arg Glu Arg Pro Ala
    370                 375                 380

Phe Ala Met Asp Arg Thr Tyr Glu Val Ser Asp Thr Lys Trp Val Gly
385                 390                 395                 400

Gly Gly Gly Gly Ala Leu Arg Cys Gly Val Ala Glu Met Val Gly Gly
                405                 410                 415

Gly Thr Pro Phe Ala Gly Asp Leu Thr Ser Lys Leu Ile Ser Tyr His
            420                 425                 430

Met Lys Cys Lys Asn Glu Asn Gly Glu Asp Ser Ile Val Val Ser Met
        435                 440                 445

Leu Leu Pro Glu Pro Ala Met Glu Arg Phe Thr Lys Glu Met Ser Phe
    450                 455                 460

Trp Leu Lys Ser Tyr
465

<210> SEQ ID NO 6
<211> LENGTH: 1410
<212> TYPE: DNA
<213> ORGANISM: Oryza sativa

<400> SEQUENCE: 6
atggtggcca ctttcacggc acgccggagc tcgccggagc tggtgacgcc ggctaggccg      60
acgccacgtg agaccaagct gctgtccgac ctcgacgacc agtggacgct gcgctactac     120
gagaccgtcg tggggttctt ccgcgtctcc cccaagatgg ccggcggcct gcccggcggc     180
gacaacatcg ccgccaaggt gatcaaggcg ccgtcgccg aggccctcgt gcactactac      240
cctgtggccg ccgccctgcg ggctctcgtc ccggcgggga caagctggc cgtggactgc      300 acggcggaag gggtggcgtt cgtcgaggcc accgccgacg tgcggctgga ggagctcggc     360
gagccgctgc tgccgccgta tccgtgtgtc gaggagttcc tcggtgatgc cggcgacact     420
agggatatcc tagacaagcc tctgctcttc ctgcaggtga ctcaactgaa atgcggtgga     480
tttgtcatcg gcctccacat gtgccactgc attttgacg ccttcggcct gctccagttc      540
atcaaaacca tagctggttt cgccggcggt gaaccaatcc catccaccat gcccgtgtgg     600
ggcagagagt cgttcttcgc agcacggaca ccaccatcct tcaccatgt ctacccggca      660 tacaagccga tcctcgacgg ccggagcagc gcaggcgacg gcgacggcga cgtcgacgat     720
gtgatgctga caactccacc tgaaaccatg gtgatgaagt acttcagctt cgggccaaaa     780
gagatctcgg ctctccggag cctgatccct gcacacctca ccagatccac cacggcattc     840
```

-continued

```
gagctgctca ccgcggtcat gtggcgatgc cgcacgtcgg cgctggggta cgagcccgat      900
cgacgcgtgc gcctcatgtt caccctgaat ctacgaggga gatggtggag ccgcgaagaa      960
gaagccgccg tgccgccggg ctactacggg aacgcgcatc tctcccccat ggtgacggcc     1020
accgtcggcg agctggcccg gcagcctctc gcggacaccg tcgagctcat gtgcagggcc     1080
aaggccggca cgacgaggga gcgcgtggag tcgatggttg atctcctggc gacatggcgg     1140
gagcggccgg cgttcgccat ggacaggacg tatgaggttt ctgacacgaa atgggtcggt     1200
ggaggaggcg gtgcgttgcg ctgtggggtg gcggagatgg tcggcggcgg cacgcctttc     1260
gccggagacc tcacctcgaa gctgataagc tatcacatga aatgcaagaa cgaaaatggg     1320
gaggactcga ttgtggtgtc gatgttgttg ccagagccag cgatggagag gttcacgaag     1380
gagatgtcgt tttggctgaa gagctattaa                                     1410
```

<210> SEQ ID NO 7
<211> LENGTH: 3260
<212> TYPE: DNA
<213> ORGANISM: Oryza sativa
<220> FEATURE:
<221> NAME/KEY: CDS
<222> LOCATION: (500)..(853)
<223> OTHER INFORMATION:
<220> FEATURE:
<221> NAME/KEY: Intron
<222> LOCATION: (854)..(1857)
<223> OTHER INFORMATION:
<220> FEATURE:
<221> NAME/KEY: CDS
<222> LOCATION: (1858)..(2853)
<223> OTHER INFORMATION:

<400> SEQUENCE: 7

```
gatcgatgcc tacatgggcg ggttttcaat tttgaaattg gttttaagc tgggtcccaa       60 attttggaaa tttcaaaaaa aatttgactg aaattatttg aaattttgaa tgaatttaaa     120
taaaatttga ccaaattcat aaaaaattga aaaaaaaacc cgaaaatttc gagctgagtt     180
ttgagctgac tggtggggga cgaaatttca aacccggcac gggcgtacct gaaaattaaa     240
taggacggca gaccaaatga atggaataaa taatactcca tcttcagcaa aaatactttg     300
tagatccttc actggccact ttaatgtgta tatatatgcc acgactcgtg ttgtgtgtat     360
gaatgcaaac cgttttgcttg ggacccagtt ctctcgaccg gccgccatcg ccatggtcac     420
cttcacggca cgtcggagca acgctgagat ggtgatgccg gcacgaccga cgccacggga     480
gacgaagacc gtgtccgac atg gac gac cac cct ggc cat ctc gtc tac atc     532
                    Met Asp Asp His Pro Gly His Leu Val Tyr Ile
                    1               5                   10 ccc ttg ctc gag ttc ttc cgc tgc cgc tgc tgc cac aac agc agc agc     580
Pro Leu Leu Glu Phe Phe Arg Cys Arg Cys Cys His Asn Ser Ser Ser
            15                  20                  25 agg gcg gtg cct ccg gcg agg gcc gtc aag gcg gcc cta gct gag gct     628
Arg Ala Val Pro Pro Ala Arg Ala Val Lys Ala Ala Leu Ala Glu Ala
        30                  35                  40 ctc gtg tgg tac tat ccg gtt gcc ggc cgg ctg cgg gag atc gcc gga     676
Leu Val Trp Tyr Tyr Pro Val Ala Gly Arg Leu Arg Glu Ile Ala Gly
45                  50                  55 ggt aag ctg gtg gtg gac tgc acg gcg gaa ggg gtg gca ttc gtc gag     724
Gly Lys Leu Val Val Asp Cys Thr Ala Glu Gly Val Ala Phe Val Glu
60                  65                  70                  75 gcc gac gcc gac gtg cgg cta gag gag ctc ggc gag ccg ttg ctg ccg     772
Ala Asp Ala Asp Val Arg Leu Glu Glu Leu Gly Glu Pro Leu Leu Pro
                80                  85                  90
```

```
ccg ttc ccg tgc gtg gag gtg ctg ttg tgc gat gcc ggc gac att ggc      820
Pro Phe Pro Cys Val Glu Val Leu Leu Cys Asp Ala Gly Asp Ile Gly
            95                  100                 105 gtt gtc gtt ggc aag cca atc gtc ttc ctg cag gtataataat gaaaatataa    873
Val Val Val Gly Lys Pro Ile Val Phe Leu Gln
        110                 115 ggcagacaac caacggtata tatatatatg agcaattcta ccatccaaca tttggtacct     933
caaggtacca tattttggag ttaaatttaa aaatatattg ttcatttgat ttttttttct     993
cacgaatatt tgagatgtaa aatttttat agaaatatac cgtcggtctc gcacaaccgt     1053
tacacgaaag tgatgtagga atgacgtcgc aagcagtatc gtacggggaa acgcgagacc   1113
gagcgactcg cgaattggaa tagcgagacc gagcggattg aaagtgaagt ctcgcggtct    1173
cgctcgttgc atgagcgaga ttagcggttt atcctaatta ttatttgtta attgttaatt    1233
aagtaattaa tcgctaatca aattgagcag ttggacattg tcgctgttcg attttgcgag    1293
accgttcggt ctcgctcatc cattccgtga daccgtgcgg tctcacgctt tttctacggg    1353
ataccacccg caacgttatt ttcatgtcac tttcgcgtaa tggttgagcg aaaccgaccg    1413
tatatttcta taaaaattt tgcatcccga atattactga gaaaaaatg attagtatat     1473 ttttaaattt aattcccata ttttgtacag aaaattttgg tatctcgaga taccaaattt    1533
tacactacaa agtctcttga ggcatcaaaa ttagtgatac ctcaggatgg taaaattgct    1593
cataatatac ccatgcatgt gtcgccacct aatcaaagcg tacactgggg gatcgtagat   1653
cgggaccgtt ttaacacaaa agtttcaccg acagaggatg acggcagaaa aaaaatctat   1713
gccaccatcg ctaccaacgt ttaaagtagt ataattagtg gttttaaatt ttacaattaa   1773
aaatgggaga accaaaattt tagaaattg aaacaagcta gattgctata ggaatatgaa    1833
ctaaattgct atgtatacat gtag gtg aca gag ttc aag tgc gga gga ttt     1884
                          Val Thr Glu Phe Lys Cys Gly Gly Phe
                              120                 125 gtg atg ggg ttc tac ata agc cac tgc atc gcc gac ggg ttc ggc atg    1932
Val Met Gly Phe Tyr Ile Ser His Cys Ile Ala Asp Gly Phe Gly Met
        130                 135                 140 atc caa ttc atc aaa gcc atc gtc gac atc gcg cga ggc gag caa gct    1980
Ile Gln Phe Ile Lys Ala Ile Val Asp Ile Ala Arg Gly Glu Gln Ala
145                 150                 155 cca atg gtg ctc ccc gtc tgg gag aga cac atc ctc aca tcc cga tca    2028
Pro Met Val Leu Pro Val Trp Glu Arg His Ile Leu Thr Ser Arg Ser
160                 165                 170                 175 cca cca cct acc att gga gct acc aat acc aat acc gtc aag ttc agc    2076
Pro Pro Pro Thr Ile Gly Ala Thr Asn Thr Asn Thr Val Lys Phe Ser
            180                 185                 190 tca gtc ctc aag gac tcc acc tcc att gac gat gac atc atg ctc tcc    2124
Ser Val Leu Lys Asp Ser Thr Ser Ile Asp Asp Asp Ile Met Leu Ser
        195                 200                 205 acg ccc caa gaa tcc atg gtc ggc aac tac ttc ctc ttt cgt ccc aac    2172
Thr Pro Gln Glu Ser Met Val Gly Asn Tyr Phe Leu Phe Arg Pro Asn
    210                 215                 220 cac atc tcc gcc ctg cga agc cat gtc cac gaa cac ggg gcg acg acg    2220
His Ile Ser Ala Leu Arg Ser His Val His Glu His Gly Ala Thr Thr
225                 230                 235 gcg acg agg ttt gag ctg atc acc gcg gtg atc tgg cgg tgc cgc acg    2268
Ala Thr Arg Phe Glu Leu Ile Thr Ala Val Ile Trp Arg Cys Arg Thr
240                 245                 250                 255 gtg gcg ctc ggc tac aag acc gac cac cgc gtc cac ttg ctg ttc gcc    2316
Val Ala Leu Gly Tyr Lys Thr Asp His Arg Val His Leu Leu Phe Ala
```

```
                 260                 265                 270
gcc aac tcg cgc cgc cac cgc ggg gac ggc acg ctc cgc atc ccg gag      2364
Ala Asn Ser Arg Arg His Arg Gly Asp Gly Thr Leu Arg Ile Pro Glu
            275                 280                 285 ggg tac tac ggc aac gcc ctc acc tac cac gtc gcc gcc gcc acc gcc      2412
Gly Tyr Tyr Gly Asn Ala Leu Thr Tyr His Val Ala Ala Ala Thr Ala
        290                 295                 300 ggc gag ctg tgc ggc acc acg ctg gct cgc acg gtg gcg ctg ata cgc      2460
Gly Glu Leu Cys Gly Thr Thr Leu Ala Arg Thr Val Ala Leu Ile Arg
    305                 310                 315 gag gcg aag ctg gac ggc acg acg gag gag cgc gtg agg tcc acc gtc      2508
Glu Ala Lys Leu Asp Gly Thr Thr Glu Glu Arg Val Arg Ser Thr Val
320                 325                 330                 335 gcc ttc ctg gcg tcg ctg cgc ctg cgc cgc agc ggc ggc cgg ttc ccg      2556
Ala Phe Leu Ala Ser Leu Arg Leu Arg Arg Ser Gly Gly Arg Phe Pro
                340                 345                 350 gcg ctg gcg ttc gac aag gcg tac gcg gtg tcc gac ttc acg agg ctc      2604
Ala Leu Ala Phe Asp Lys Ala Tyr Ala Val Ser Asp Phe Thr Arg Leu
            355                 360                 365 ggc gag gac ggg ctg gat ttc ggg tgg gcg gag cgc gtg ggc ggc ggc      2652
Gly Glu Asp Gly Leu Asp Phe Gly Trp Ala Glu Arg Val Gly Gly Gly
        370                 375                 380 gtg gcc acg ccg tcg ttc gtg agc ttc cac agc agg tgg aag ctg gtg      2700
Val Ala Thr Pro Ser Phe Val Ser Phe His Ser Arg Trp Lys Leu Val
    385                 390                 395 agc tct gac ggc gat ggc gag gaa gaa gaa gct gtt gct gcg ttg atg      2748
Ser Ser Asp Gly Asp Gly Glu Glu Glu Glu Ala Val Ala Ala Leu Met
400                 405                 410                 415 ctg ctg ccg aag ccg gcc atg gat agg ttc gac aag gag ttg gca tta      2796
Leu Leu Pro Lys Pro Ala Met Asp Arg Phe Asp Lys Glu Leu Ala Leu
                420                 425                 430 tgg ttg gac ttg gac aag cca tca gtt gga ggc ctc tgc ctc tcc agc      2844
Trp Leu Asp Leu Asp Lys Pro Ser Val Gly Gly Leu Cys Leu Ser Ser
            435                 440                 445 aaa ttt tga tataaaa gcgccgcaat taaaaaaaaa gaagcaagtg ttgattcttc      2900
Lys Phe tccatgcact tcaccttgct tgagttcaat caaaagcttc attttgtatt gaaaaaaata   2960
aaatattcgt tttgagatat accggcacag tttactgtgt gtgtagtata tgtaaaatca   3020
tgatgatgat taatttgtaa cgaattatac cctggctgat tttaacttta tcaatattat   3080
gttgtatcga ttgggttcga cctatagatg gctatatggc ctgagcccgc ggcccggccc   3140
aagcatggca cagcccgaca gccgagtcgt gccagggctg caccctcggc acgatgggcc   3200
gacccggcac ggcacgatcg aagaaaaata gtataaggat gaaaaataaa cttaataac    3260
```

<210> SEQ ID NO 8
<211> LENGTH: 449
<212> TYPE: PRT
<213> ORGANISM: Oryza sativa

<400> SEQUENCE: 8

Met Asp Asp His Pro Gly His Leu Val Tyr Ile Pro Leu Leu Glu Phe
1               5                   10                  15

Phe Arg Cys Arg Cys Cys His Asn Ser Ser Arg Ala Val Pro Pro
            20                  25                  30

Ala Arg Ala Val Lys Ala Ala Leu Ala Glu Ala Leu Val Trp Tyr Tyr
        35                  40                  45

Pro Val Ala Gly Arg Leu Arg Glu Ile Ala Gly Gly Lys Leu Val Val

-continued

```
             50                 55                  60
Asp Cys Thr Ala Glu Gly Val Ala Phe Val Glu Ala Asp Ala Asp Val
 65                  70                  75                  80

Arg Leu Glu Glu Leu Gly Glu Pro Leu Leu Pro Pro Phe Pro Cys Val
                     85                  90                  95

Glu Val Leu Leu Cys Asp Ala Gly Asp Ile Gly Val Val Gly Lys
                100                 105                 110

Pro Ile Val Phe Leu Gln Val Thr Glu Phe Lys Cys Gly Gly Phe Val
                115                 120                 125

Met Gly Phe Tyr Ile Ser His Cys Ile Ala Asp Gly Phe Gly Met Ile
    130                 135                 140

Gln Phe Ile Lys Ala Ile Val Asp Ile Ala Arg Gly Glu Gln Ala Pro
145                 150                 155                 160

Met Val Leu Pro Val Trp Glu Arg His Ile Leu Thr Ser Arg Ser Pro
                165                 170                 175

Pro Pro Thr Ile Gly Ala Thr Asn Thr Asn Thr Val Lys Phe Ser Ser
                180                 185                 190

Val Leu Lys Asp Ser Thr Ser Ile Asp Asp Ile Met Leu Ser Thr
            195                 200                 205

Pro Gln Glu Ser Met Val Gly Asn Tyr Phe Leu Phe Arg Pro Asn His
    210                 215                 220

Ile Ser Ala Leu Arg Ser His Val His Glu His Gly Ala Thr Thr Ala
225                 230                 235                 240

Thr Arg Phe Glu Leu Ile Thr Ala Val Ile Trp Arg Cys Arg Thr Val
                245                 250                 255

Ala Leu Gly Tyr Lys Thr Asp His Arg Val His Leu Leu Phe Ala Ala
                260                 265                 270

Asn Ser Arg Arg His Arg Gly Asp Gly Thr Leu Arg Ile Pro Glu Gly
            275                 280                 285

Tyr Tyr Gly Asn Ala Leu Thr Tyr His Val Ala Ala Ala Thr Ala Gly
    290                 295                 300

Glu Leu Cys Gly Thr Thr Leu Ala Arg Thr Val Ala Leu Ile Arg Glu
305                 310                 315                 320

Ala Lys Leu Asp Gly Thr Thr Glu Glu Arg Val Arg Ser Thr Val Ala
                325                 330                 335

Phe Leu Ala Ser Leu Arg Leu Arg Arg Ser Gly Gly Arg Phe Pro Ala
                340                 345                 350

Leu Ala Phe Asp Lys Ala Tyr Ala Val Ser Asp Phe Thr Arg Leu Gly
            355                 360                 365

Glu Asp Gly Leu Asp Phe Gly Trp Ala Glu Arg Val Gly Gly Gly Val
    370                 375                 380

Ala Thr Pro Ser Phe Val Ser Phe His Ser Arg Trp Lys Leu Val Ser
385                 390                 395                 400

Ser Asp Gly Asp Gly Glu Glu Glu Ala Val Ala Leu Met Leu
                405                 410                 415

Leu Pro Lys Pro Ala Met Asp Arg Phe Asp Lys Glu Leu Ala Leu Trp
            420                 425                 430

Leu Asp Leu Asp Lys Pro Ser Val Gly Gly Leu Cys Leu Ser Ser Lys
            435                 440                 445

Phe

<210> SEQ ID NO 9
<211> LENGTH: 1350
```

<212> TYPE: DNA
<213> ORGANISM: Oryza sativa

<400> SEQUENCE: 9

```
atggacgacc accctggcca tctcgtctac atcccttgc tcgagttctt ccgctgccgc      60
tgctgccaca acagcagcag cagggcggtg cctccggcga gggccgtcaa ggcggcccta    120
gctgaggctc tcgtgtggta ctatccggtt gccggccggc tgcgggagat cgccggaggt    180
aagctggtgg tggactgcac ggcggaaggg gtggcattcg tcgaggccga cgccgacgtg    240
cggctagagg agctcggcga gccgttgctg ccgccgttcc cgtgcgtgga ggtgctgttg    300
tgcgatgccg gcgacattgg cgttgtcgtt ggcaagccaa tcgtcttcct gcaggtgaca    360
gagttcaagt gcggaggatt tgtgatgggg ttctacataa gccactgcat cgccgacggg    420
ttcggcatga tccaattcat caaagccatc gtcgacatcg cgcgaggcga gcaagctcca    480
atggtgctcc ccgtctggga gagacacatc ctcacatccc gatcaccacc acctaccatt    540
ggagctacca ataccaatac cgtcaagttc agctcagtcc tcaaggactc cacctccatt    600
gacgatgaca tcatgctctc cacgccccaa gaatccatgg tcggcaacta cttcctcttt    660
cgtcccaacc acatctccgc cctgcgaagc catgtccacg aacacggggc gacgacggcg    720
acgaggtttg agctgatcac cgcggtgatc tggcggtgcc gcacggtggc gctcggctac    780
aagaccgacc accgcgtcca cttgctgttc gccgccaact cgcgccgcca ccgcggggac    840
ggcacgctcc gcatcccgga ggggtactac ggcaacgccc tcacctacca cgtcgccgcc    900
gccaccgccg gcgagctgtg cggcaccacg ctggctcgca cggtgcgcgt gatacgcgag    960
gcgaagctgg acggcacgac ggaggagcgc gtgaggtcca ccgtcgcctt cctggcgtcg   1020
ctgcgcctgc gccgcagcgg cggccggttc ccggcgctgg cgttcgacaa ggcgtacgcg   1080
gtgtccgact tcacgaggct cggcgaggac gggctggatt tcgggtgggc ggagcgcgtg   1140
ggcggcggcg tggccacgcc gtcgttcgtg agcttccaca gcaggtggaa gctggtgagc   1200
tctgacggcg atggcgagga agaagaagct gttgctgcgt tgatgctgct gccgaagccg   1260
gccatggata ggttcgacaa ggagttggca ttatggttgg acttggacaa gccatcagtt   1320
ggaggcctct gcctctccag caaattttga                                     1350
```

<210> SEQ ID NO 10
<211> LENGTH: 4850
<212> TYPE: DNA
<213> ORGANISM: Oryza sativa
<220> FEATURE:
<221> NAME/KEY: CDS
<222> LOCATION: (507)..(1845)
<223> OTHER INFORMATION:
<220> FEATURE:
<221> NAME/KEY: Intron
<222> LOCATION: (1846)..(4180)
<223> OTHER INFORMATION:
<220> FEATURE:
<221> NAME/KEY: CDS
<222> LOCATION: (4181)..(4449)
<223> OTHER INFORMATION:

<400> SEQUENCE: 10

```
aaaattaaga gttagatatt cttctctttt ttagattttt gtttaaatta ttagagcgcc      60
gcgtggcggc ttgagggcgt ttgtagaaag tttaatggaa ttttaatata taatagataa    120
gttaatagat tttgaagtca aagtttctgt agcatagctg tcatcgtgtt gaagggtaat    180
acaatataat gtatgctttt tgcgtgttat taattacgtc catgtttttt agttggtagg    240
```

-continued

```
tttcatggga gttgagagtt gagatagtga gcagattgta aatttgtact aatgtgtatg    300
ttggattgaa tgattgattg taaattaggt tgaataattg atatatacta tacatatgaa    360
aaatttaaat ctcagggccc caatttgcat atcaccatga ggccccagag tggtagagac    420
agccgccctg cttttatat atacacgcgc atgcaccctg ctaaataaaa ttgcaagcct     480
gagcgggtcg gagcatgtat actacc atg gcg agt agg agt agg ttg gta gca    533
                            Met Ala Ser Arg Ser Arg Leu Val Ala
                              1               5 cgt cgg agc aag cct gag ctg gtg gcg ccg tca cgg ccg acg cca cac    581
Arg Arg Ser Lys Pro Glu Leu Val Ala Pro Ser Arg Pro Thr Pro His
 10              15                  20                  25 gaa acc aag ctt ctc tcc gac ctc gac gat ttc cgc aac cac tac gag    629
Glu Thr Lys Leu Leu Ser Asp Leu Asp Asp Phe Arg Asn His Tyr Glu
                 30                  35                  40 tac acc cca ctc gtc gcc ttc ttc cgc agc tcc ggc tcc ggc aac gac    677
Tyr Thr Pro Leu Val Ala Phe Phe Arg Ser Ser Gly Ser Gly Asn Asp
                 45                  50                  55 gtc cca tcg ccg ccg acg atg acc atc cgg aca gca att ggg gag gcg    725
Val Pro Ser Pro Pro Thr Met Thr Ile Arg Thr Ala Ile Gly Glu Ala
         60                  65                  70 ctc gtg tac tac tac cca ctg gcc ggc cgc ctg cgc gag ctt ccc tgc    773
Leu Val Tyr Tyr Tyr Pro Leu Ala Gly Arg Leu Arg Glu Leu Pro Cys
         75                  80                  85 ggc aag ctg gtg gtg gac tgc acc gag gaa ggg gtg gtg ttc gtc gcc    821
Gly Lys Leu Val Val Asp Cys Thr Glu Glu Gly Val Val Phe Val Ala
 90              95                  100                 105 gcc gag gct gac ctg cgc ctc gct gac ctc ggc gag cca ctg ctg ctg    869
Ala Glu Ala Asp Leu Arg Leu Ala Asp Leu Gly Glu Pro Leu Leu Leu
                 110                 115                 120 cca ttc ccg tgc tct ggc gag ctg ctc gtc tgc gac aac gcg aga tca    917
Pro Phe Pro Cys Ser Gly Glu Leu Leu Val Cys Asp Asn Ala Arg Ser
                 125                 130                 135 gat agc ctg cat gtc gcc gtc gtt gac aag cca ttg atc ttc atg cag    965
Asp Ser Leu His Val Ala Val Val Asp Lys Pro Leu Ile Phe Met Gln
         140                 145                 150 gtg acg gaa ttc aaa tgt gga gga ttt gcc att gcc atg caa ggg aac   1013
Val Thr Glu Phe Lys Cys Gly Gly Phe Ala Ile Ala Met Gln Gly Asn
         155                 160                 165 cac tgc gtc gcc gat ggt ttt ggg gcc agc cag ttc atg aac gcc atc   1061
His Cys Val Ala Asp Gly Phe Gly Ala Ser Gln Phe Met Asn Ala Ile
170                 175                 180                 185 gcc gac ctc gct cgc ggc gag ccg cgc ccg ctc gtg ctc ccc gtg tgg   1109
Ala Asp Leu Ala Arg Gly Glu Pro Arg Pro Leu Val Leu Pro Val Trp
                 190                 195                 200 gag agg cac ctc gtc atg gcg cgc gcg cca ccc agc gtc gcc gcc gcg   1157
Glu Arg His Leu Val Met Ala Arg Ala Pro Pro Ser Val Ala Ala Ala
         205                 210                 215 tac ccg gcg ttc aag ccg ctc atc gac ggc gcc agc agc aac gac gtg   1205
Tyr Pro Ala Phe Lys Pro Leu Ile Asp Gly Ala Ser Ser Asn Asp Val
         220                 225                 230 atg ctc tcc acg ccg ctt gac acc atg gtg acc cgg cac ttc ctg ttc   1253
Met Leu Ser Thr Pro Leu Asp Thr Met Val Thr Arg His Phe Leu Phe
         235                 240                 245 ggc cgg cga gag atg gcc gcg cta cgg cgc ctc ctc ccc gcg cgc ctc   1301
Gly Arg Arg Glu Met Ala Ala Leu Arg Arg Leu Leu Pro Ala Arg Leu
250                 255                 260                 265 ggc cgg cgc tgc acg gac ttc cag ctg ctc gcc gcc acg ctg tgg cgg   1349
Gly Arg Arg Cys Thr Asp Phe Gln Leu Leu Ala Ala Thr Leu Trp Arg
                 270                 275                 280
```

-continued

```
tgc cgc acg gcg gcg ctg ccc tac gcc ccg cac cgg cga gtg cat gcc    1397
Cys Arg Thr Ala Ala Leu Pro Tyr Ala Pro His Arg Arg Val His Ala
        285                 290                 295 tac ctc ccc ctt agc atg cac gga aga cgg tgg cta cac atc ccg gaa    1445
Tyr Leu Pro Leu Ser Met His Gly Arg Arg Trp Leu His Ile Pro Glu
    300                 305                 310 ggg tac tac ggc aac gcg ctc gcc tac tcc att gcc gac gcc agc gcc    1493
Gly Tyr Tyr Gly Asn Ala Leu Ala Tyr Ser Ile Ala Asp Ala Ser Ala
315                 320                 325 ggc gat ctg tgc ggt ggg acg cta ggg cag acg gtg gag cag gtc tgc    1541
Gly Asp Leu Cys Gly Gly Thr Leu Gly Gln Thr Val Glu Gln Val Cys
330                 335                 340                 345 gag gcg agg cta cag gtg acg ggg gag tac gtg aga tcg acg gtg gac    1589
Glu Ala Arg Leu Gln Val Thr Gly Glu Tyr Val Arg Ser Thr Val Asp
                350                 355                 360 ttg atg gcg tcg ctg cgt ggg cgc ggc atg gtg ttc gac ggg gtg tac    1637
Leu Met Ala Ser Leu Arg Gly Arg Gly Met Val Phe Asp Gly Val Tyr
            365                 370                 375 gtg gtg tcg gac ctg agg cgg ctc ttc gca gag ctg gac ttt ggg tgc    1685
Val Val Ser Asp Leu Arg Arg Leu Phe Ala Glu Leu Asp Phe Gly Cys
        380                 385                 390 gga gag tgg gtg gtc agc ggc atg gcg cag ccg atg ctg gcg acg ttc    1733
Gly Glu Trp Val Val Ser Gly Met Ala Gln Pro Met Leu Ala Thr Phe
    395                 400                 405 ctg gtg agg tgc agg aac gcc gac ggc gag gac gcg gtg gca gcg tcg    1781
Leu Val Arg Cys Arg Asn Ala Asp Gly Glu Asp Ala Val Ala Ala Ser
410                 415                 420                 425 atg ctg ttg ccg cct tcg gtg atg gag agg ttt gca gag gag ctt gct    1829
Met Leu Leu Pro Pro Ser Val Met Glu Arg Phe Ala Glu Glu Leu Ala
                430                 435                 440 ggg ctg atg atg agc a gtaagcacga caactccagc ccccgacttt agagtctaga  1885
Gly Leu Met Met Ser
                445 tgaatacagg gttctgggat tcggaccgaa tggtctgaat tttgacgaat tcatccatt   1945
tcgatcggtg aggtccgaga gaatatgtca cttccatttc atctcaactt ggttcaaatt  2005
tggtcagatt tatcaaattc gaccatgaaa attacaaaat ccgttcattt ctgtgggccc  2065
tgaacatttg ttttccaatc atatcctggt acctcgatga atatcgtctt tactactcaa  2125
gataatgtat accgttaaat atctttatct ttatctatct aaaaaattga ggatgcttct  2185
gtactcacag caccttgatc cgtcgtcgcc tcttcgtaag cacgcgacac agcgcaactg  2245
tccaatcgtc ctccgtttag atcgagctgt caacactgca cgatgaaggg aatggaccgc  2305
acggcattga tgcccacatc tcaaacacac gtggatttcc gccgctcgga tcgtgtgaag  2365
gcaatataag agtgtgaact catggtgaaa atggcattta tacccagccc attcgaaaga  2425
tagataacaa acaagtaccc tataaaacaa atttcggaga acagataggc gtagagctac  2485
tctgttcagt gcatgatcat aatctagaac tgtctccatt agatcccatc ttctatatta  2545
ccgctgataa actaagtcct gctaagattt tagacgtgtg ctacgtttta tcatagtatt  2605
agccagtaag ttatctttac attggacttc cagatgatct atactttaac catcgagttg  2665
acatttaata ttatctatca atatcggccg attgattcat tgtacatcta tttcatcata  2725
ttattattgg ccgattggat tgttcattat ctttatctaa gtgttcaaat ctacatcgga  2785
tatatagacg attgtttaaa accctattga catcggctag tatcactaca tcggtttatt  2845
ggccgatcgg cggctagtat cactacatcg gtttattgcc gatcagctat ttgatcatca  2905
```

-continued

```
atttatctat gctgtcagtt gcagaatcaa atttactaac acgcccgata ttataggaac      2965
tgcactggag ttaagcaaat ctcctaagcc ttttgtgtgt cacgacaaaa tttcatgcga      3025
acactagcgt ggcagtaaat ctccctgttc tttgtgtgtc acgaggaaat ttcacgtgaa      3085
caccagcgtg gcactcatgc gtgtgtggta gtccgaccac tatctgaacc acttaacagg      3145
tgctattgat tagcaacctg tttaagtcgg ggtctctccg tgttggtttt aaaggtggta      3205
tctgtagccg ggctatatcc tccatatttt tttatgacgc tccaattcac tccaaaagtg      3265 tttttattt gacgttcgta attctttatc cactcctccc gtgagcgaat ttccttcctt      3325 ccccctccc ctcccacccg cgcgatgcca ccttcgtgac caccgaatca tcgatgcttc      3385
tcactataga tggccaaaat gggccgcccg ccccagcaca gactaggccc ggtcgtgccc      3445
gggctggcac ggcccaacct acacgtcggg tcgtgtcgtg ccggcccaca tgctccacct      3505
attgcctagg catggccagg ccggtccgaa ggcacaggca gcccatcgtg ctttctttga      3565
aataagtcta tttcccctcc ctcctctttg ggttatgacg tgtatttgtg tgtgtgtgta      3625
tatatatata tatatatata tatatatata tatatatata tatatatata tatatatata      3685
tatatatata aagtaagtct attttgcatc ctactctttg ggctgtgtca tataatacgt      3745
cgttttgtcc ttcctattcc tattctttgt gtcctatctt ttcatatggt tgaaaataag      3805
tctatatcac ctccctgaac tttgtgccat gccggatcag cccaccatgc cgaggcatag      3865
gcccagacac ggcccaataa acgggccgtg ctgtgcctag gccaggccaa aacctcgtgc      3925
ctcgcgccgg gccgttgggc ctcgggtctt atggcgagta tacttctcac caccgctgcc      3985
gtctcctcct aaacagcgcc tcttcctgta ggcagcagcc gctgctcatt cgccgacgat      4045
gacacctcct cttcgtcaag cgtcgcctcc ggactcgcct cgtaatacct cctccaggtc      4105
tgacttcccc ttccttcttc cgttcttctt gctatgtttg gtctgatctc tgactgtgtc      4165
ttgttcttga tgcag ag  gag gaa tat gaa gac gaa cga gtt cat cac ggt       4215
                    Lys Glu Glu Tyr Glu Asp Glu Arg Val His His Gly
                    450                 455 gtt gcc agt ctt cat gtg cgt gat cct cgt tgt gct gca ggg gat gct       4263
Val Ala Ser Leu His Val Arg Asp Pro Arg Cys Ala Ala Gly Asp Ala
460                 465                 470 caa cca cga gct caa caa gcc aaa gta cca gtg cag tac ggc tgc gcc       4311
Gln Pro Arg Ala Gln Gln Ala Lys Val Pro Val Gln Tyr Gly Cys Ala
475                 480                 485                 490 tgc gtc gag cac tcg acg ctg gac cag ctg gtt ggc agc tgc ctg atc       4359
Cys Val Glu His Ser Thr Leu Asp Gln Leu Val Gly Ser Cys Leu Ile
                495                 500                 505 ccg agc ccg acg ccc tgg ctg acc ctg ttc cgg cca ggt ccc ccg ccc       4407
Pro Ser Pro Thr Pro Trp Leu Thr Leu Phe Arg Pro Gly Pro Pro Pro
        510                 515                 520 cga gtc agg atc gcc tcc cca gcc gtt cga tgg ttt gcc tga cctgaac     4456
Arg Val Arg Ile Ala Ser Pro Ala Val Arg Trp Phe Ala
        525                 530                 535 tgcaggggcg ccgtctggag caaataactg tgtagaatca gaacatgaga cttacaactt      4516 ctctttttc aggaattgga cttcaaaatt agaatagcat tttcataatc tatgaattca      4576
taatcataaa ggttgggttt caatttggga agtttcaggt tgtgatactg tcttgtggtg      4636
ttgattgggt tacagtgatg gactgatagc catggacctg aaaatgagtt tgtaatatgg      4696
aataatgtcg gtggttgtaa ctgtttgtaa cttggagttt gttggcaggg aagattattc      4756
agaggcgttg tcagaaaaca tttcagtttc agctctctgg aactgaccaa gggatttggt      4816
ttctaaattt ccagggcgat aacgaaatac tgac                                 4850
```

<210> SEQ ID NO 11
<211> LENGTH: 535
<212> TYPE: PRT
<213> ORGANISM: Oryza sativa

<400> SEQUENCE: 11

Met Ala Ser Arg Ser Arg Leu Val Ala Arg Ser Lys Pro Glu Leu
1               5                   10                  15

Val Ala Pro Ser Arg Pro Thr Pro His Glu Thr Lys Leu Leu Ser Asp
            20                  25                  30

Leu Asp Asp Phe Arg Asn His Tyr Glu Tyr Thr Pro Leu Val Ala Phe
        35                  40                  45

Phe Arg Ser Ser Gly Ser Gly Asn Asp Val Pro Ser Pro Pro Thr Met
    50                  55                  60

Thr Ile Arg Thr Ala Ile Gly Glu Ala Leu Val Tyr Tyr Tyr Pro Leu
65                  70                  75                  80

Ala Gly Arg Leu Arg Glu Leu Pro Cys Gly Lys Leu Val Val Asp Cys
                85                  90                  95

Thr Glu Glu Gly Val Val Phe Val Ala Ala Glu Ala Asp Leu Arg Leu
            100                 105                 110

Ala Asp Leu Gly Glu Pro Leu Leu Leu Pro Phe Pro Cys Ser Gly Glu
        115                 120                 125

Leu Leu Val Cys Asp Asn Ala Arg Ser Asp Ser Leu His Val Ala Val
    130                 135                 140

Val Asp Lys Pro Leu Ile Phe Met Gln Val Thr Glu Phe Lys Cys Gly
145                 150                 155                 160

Gly Phe Ala Ile Ala Met Gln Gly Asn His Cys Val Ala Asp Gly Phe
                165                 170                 175

Gly Ala Ser Gln Phe Met Asn Ala Ile Ala Asp Leu Ala Arg Gly Glu
            180                 185                 190

Pro Arg Pro Leu Val Leu Pro Val Trp Glu Arg His Leu Val Met Ala
        195                 200                 205

Arg Ala Pro Pro Ser Val Ala Ala Tyr Pro Ala Phe Lys Pro Leu
    210                 215                 220

Ile Asp Gly Ala Ser Ser Asn Asp Val Met Leu Ser Thr Pro Leu Asp
225                 230                 235                 240

Thr Met Val Thr Arg His Phe Leu Phe Gly Arg Arg Glu Met Ala Ala
                245                 250                 255

Leu Arg Arg Leu Leu Pro Ala Arg Leu Gly Arg Arg Cys Thr Asp Phe
            260                 265                 270

Gln Leu Leu Ala Ala Thr Leu Trp Arg Cys Arg Thr Ala Ala Leu Pro
        275                 280                 285

Tyr Ala Pro His Arg Arg Val His Ala Tyr Leu Pro Leu Ser Met His
    290                 295                 300

Gly Arg Arg Trp Leu His Ile Pro Glu Gly Tyr Tyr Gly Asn Ala Leu
305                 310                 315                 320

Ala Tyr Ser Ile Ala Asp Ala Ser Ala Gly Asp Leu Cys Gly Gly Thr
                325                 330                 335

Leu Gly Gln Thr Val Glu Gln Val Cys Glu Ala Arg Leu Gln Val Thr
            340                 345                 350

Gly Glu Tyr Val Arg Ser Thr Val Asp Leu Met Ala Ser Leu Arg Gly
        355                 360                 365

Arg Gly Met Val Phe Asp Gly Val Tyr Val Val Ser Asp Leu Arg Arg

```
                370                 375                 380
Leu Phe Ala Glu Leu Asp Phe Gly Cys Gly Glu Trp Val Val Ser Gly
385                 390                 395                 400

Met Ala Gln Pro Met Leu Ala Thr Phe Leu Val Arg Cys Arg Asn Ala
                405                 410                 415

Asp Gly Glu Asp Ala Val Ala Ala Ser Met Leu Leu Pro Pro Ser Val
                420                 425                 430

Met Glu Arg Phe Ala Glu Glu Leu Ala Gly Leu Met Met Ser Lys Glu
                435                 440                 445

Glu Tyr Glu Asp Glu Arg Val His His Gly Val Ala Ser Leu His Val
450                 455                 460

Arg Asp Pro Arg Cys Ala Ala Gly Asp Ala Gln Pro Arg Ala Gln Gln
465                 470                 475                 480

Ala Lys Val Pro Val Gln Tyr Gly Cys Ala Cys Val Glu His Ser Thr
                485                 490                 495

Leu Asp Gln Leu Val Gly Ser Cys Leu Ile Pro Ser Pro Thr Pro Trp
                500                 505                 510

Leu Thr Leu Phe Arg Pro Gly Pro Pro Arg Val Arg Ile Ala Ser
                515                 520                 525

Pro Ala Val Arg Trp Phe Ala
    530                 535

<210> SEQ ID NO 12
<211> LENGTH: 1608
<212> TYPE: DNA
<213> ORGANISM: Oryza sativa

<400> SEQUENCE: 12
atggcgagta ggagtaggtt ggtagcacgt cggagcaagc ctgagctggt ggcgccgtca      60
cggccgacgc cacacgaaac caagcttctc tccgacctcg acgatttccg caaccactac     120
gagtacaccc cactcgtcgc cttcttccgc agctccggct ccggcaacga cgtcccatcg     180
ccgccgacga tgaccatccg gacagcaatt ggggaggcgc tcgtgtacta ctacccactg     240
gccggccgcc tgcgcgagct ccctgcggc aagctggtgg tggactgcac cgaggaaggg      300
gtggtgttcg tcgccgccga ggctgacctg cgcctcgctg acctcggcga gccactgctg     360
ctgccattcc cgtgctctgg cgagctgctc gtctgcgaca cgcgagatc agatagcctg      420 catgtcgccg tcgttgacaa gccattgatc ttcatgcagg tgacggaatt caaatgtgga     480
ggatttgcca ttgccatgca agggaaccac tgcgtcgccg atggttttgg ggccagccag     540
ttcatgaacg ccatcgccga cctcgctcgc ggcgagccgc gccgctcgt gctcccgtg       600 tgggagaggc acctcgtcat ggcgcgcgcg ccacccagcg tcgccgccgc gtacccggcg     660
ttcaagccgc tcatcgacgg cgccagcagc aacgacgtga tgctctccac gccgcttgac     720
accatggtga cccggcactt cctgttcggc cggcgagaga tggccgcgct acggcgcctc     780
ctccccgcgc gcctcggccg gcgctgcacg gacttccagc tgctcgccgc cacgctgtgg     840
cggtgccgca cggcggcgct gccctacgcc cgcaccggc gagtgcatgc ctacctcccc      900
cttagcatgc acggaagacg gtggctacac atcccggaag gtactacgg caacgcgctc      960 gcctactcca ttgccgacgc cagcgccggc gatctgtgcg gtgggacgct agggcagacg    1020
gtggagcagg tctgcgaggc gaggctacag gtgacggggg agtacgtgag atcgacggtg    1080
gacttgatgg cgtcgctgcg tgggcgcggc atggtgttcg acggggtgta cgtggtgtcg    1140
gacctgaggc ggctcttcgc agagctggac tttgggtgcg gagagtgggt ggtcagcggc    1200
```

```
atggcgcagc cgatgctggc gacgttcctg gtgaggtgca ggaacgccga cggcgaggac      1260
gcggtggcag cgtcgatgct gttgccgcct tcggtgatgg agaggtttgc agaggagctt      1320
gctgggctga tgatgagcaa ggaggaatat gaagacgaac gagttcatca cggtgttgcc      1380
agtcttcatg tgcgtgatcc tcgttgtgct gcagggatg ctcaaccacg agctcaacaa      1440
gccaaagtac cagtgcagta cggctgcgcc tgcgtcgagc actcgacgct ggaccagctg      1500
gttggcagct gcctgatccc gagcccgacg ccctggctga ccctgttccg gccaggtccc      1560
ccgccccgag tcaggatcgc ctccccagcc gttcgatggt ttgcctga                   1608
```

<210> SEQ ID NO 13
<211> LENGTH: 2200
<212> TYPE: DNA
<213> ORGANISM: Oryza sativa
<220> FEATURE:
<221> NAME/KEY: CDS
<222> LOCATION: (499)..(1803)
<223> OTHER INFORMATION:

<400> SEQUENCE: 13

```
ttttgcgtgt aattaattac gttcatattt taagtgtgtt ttttagttgg ttggtatcat       60
gggagttgag agttgagata gtgagcagat tgtaaatttg aaatgtataa gttggattga      120
attattgatt ctaaattaga ttgaataatt gatatatact atacatatga aaatttcacc      180
aaatttcaaa tgagcaatgc tacacgtact aaattttttct tactaaattt ttactaacaa    240
tcatctcaac cgtttgattt aagtagatgg aagttacaaa aaatctagat gcactcgtag      300
catgacacat cagtgttagt aagaaattag taagaaaaag ttagtacgta tagccttttc      360
catttcaaat cttagggtcc caatttgcat atcacccgag gccccaaatt cttagagacg      420
gccgccctgc ttttatata tacacgcgca ccctgctaaa taaaattgca agcctgagct       480
cgtcggagaa tgtatacc atg gcg agt cgg agt agg ctg gtg gca cgt cgg      531
                              Met Ala Ser Arg Ser Arg Leu Val Ala Arg Arg
                                1               5                  10
          agc aag cct gag ctg gtg gcg ccg tca cgc cgc acg ccg cac gac acc      579
          Ser Lys Pro Glu Leu Val Ala Pro Ser Arg Arg Thr Pro His Asp Thr
                  15                  20                  25
          aag ctt ctc tcc gac ctc gac gat ttc cgc aac cac tac gag tac acc      627
          Lys Leu Leu Ser Asp Leu Asp Asp Phe Arg Asn His Tyr Glu Tyr Thr
                      30                  35                  40
          cca ctt gtc gcc ttc ttc cgc acc tcc agc acc ggc aac atc ccg tcg      675
          Pro Leu Val Ala Phe Phe Arg Thr Ser Ser Thr Gly Asn Ile Pro Ser
               45                  50                  55
          gcg ccg cca ccg gag atg acc atc cgg aga gca att gcg gag gcg ctc      723
          Ala Pro Pro Pro Glu Met Thr Ile Arg Arg Ala Ile Ala Glu Ala Leu
          60                  65                  70                  75
          gtg tac tac tac cca cta gcc ggc cgc ctg cgc gag ctt ccc tgc ggc      771
          Val Tyr Tyr Tyr Pro Leu Ala Gly Arg Leu Arg Glu Leu Pro Cys Gly
                          80                  85                  90
          aag ctg gtg gtg gac tgc acc gag gaa ggg gtg gtg ttc gtc gcc gcc      819
          Lys Leu Val Val Asp Cys Thr Glu Glu Gly Val Val Phe Val Ala Ala
                          95                 100                 105
          gag gct gac ctg cgc ctc gct gac ctc ggc gag cca ctg ctc ctg cca      867
          Glu Ala Asp Leu Arg Leu Ala Asp Leu Gly Glu Pro Leu Leu Leu Pro
                     110                 115                 120
          ttc ccg tgc tcc ggc gag ctg ctc gtc tgc gac aat gtg gga gac agc      915
          Phe Pro Cys Ser Gly Glu Leu Leu Val Cys Asp Asn Val Gly Asp Ser
                 125                 130                 135
          caa gtc gcc gtc gtt gcc aag cca ttg atc ttc atg cag gtg acg gaa      963
          Gln Val Ala Val Val Ala Lys Pro Leu Ile Phe Met Gln Val Thr Glu
          140                 145                 150                 155
          ttc aaa tgc gga gga ttt gcc gtt gcc atg caa tgg aac cac tgt gtc     1011
          Phe Lys Cys Gly Gly Phe Ala Val Ala Met Gln Trp Asn His Cys Val
                             160                 165                 170
          gcc gat ggt ttt ggg gcc agc cag ttc atg aac gcc atc gcc gac ctc     1059
          Ala Asp Gly Phe Gly Ala Ser Gln Phe Met Asn Ala Ile Ala Asp Leu
                         175                 180                 185
```

```
            gct cgc ggc gag ccg cgc ccg ctc gtg ctc ccc gtg tgg gag agg cac    1107
            Ala Arg Gly Glu Pro Arg Pro Leu Val Leu Pro Val Trp Glu Arg His
                190                 195                 200
            ctc gtc atg gcg cgc gcg cca ccc agc gtc gcc gcc tac ccg gcg        1155
            Leu Val Met Ala Arg Ala Pro Pro Ser Val Ala Ala Tyr Pro Ala
                205                 210                 215
            ttc aag ccg ctc atc gac ggc gcc agc agc aac gac gtg atg ctc tcc    1203
            Phe Lys Pro Leu Ile Asp Gly Ala Ser Ser Asn Asp Val Met Leu Ser
            220                 225                 230                 235
            acg ccg ctt gac acc atg gtg acc cgg cac ttc ctg ttc ggc cgg cga    1251
            Thr Pro Leu Asp Thr Met Val Thr Arg His Phe Leu Phe Gly Arg Arg
                                240                 245                 250
            gag atg gcc gcg cta cgg cgc ctc ctc ccc gca ccc ctc ggc cgg cgc    1299
            Glu Met Ala Ala Leu Arg Arg Leu Leu Pro Ala Pro Leu Gly Arg Arg
                            255                 260                 265
            tgc acg gac ttc cag ctg ctc ccc gcc gcg cta tgg cgg tgc cgc acg    1347
            Cys Thr Asp Phe Gln Leu Leu Pro Ala Ala Leu Trp Arg Cys Arg Thr
                        270                 275                 280
            gcg gcg ctg ccc tac gcc ccg cac cgg cga gtg cgt gcc tac ctc ccc    1395
            Ala Ala Leu Pro Tyr Ala Pro His Arg Arg Val Arg Ala Tyr Leu Pro
                    285                 290                 295
            ctg agc acg cgc ggg aga cgg tgg cgc agc cag ggg ctg cac atc ccg    1443
            Leu Ser Thr Arg Gly Arg Arg Trp Arg Ser Gln Gly Leu His Ile Pro
            300                 305                 310                 315
            gag ggg tac tac ggc aac gcg ctc gcc tac tcc atc gcc aac gcc agc    1491
            Glu Gly Tyr Tyr Gly Asn Ala Leu Ala Tyr Ser Ile Ala Asn Ala Ser
                                320                 325                 330
            gcc ggc gat ctg tgc ggc ggg acg ctg ggg cag acg gtg gag ctg gtc    1539
            Ala Gly Asp Leu Cys Gly Gly Thr Leu Gly Gln Thr Val Glu Leu Val
                            335                 340                 345
            tgc gag gcg agg cta cag gtg acg ggg gag tac gtg aga tcg acg gtg    1587
            Cys Glu Ala Arg Leu Gln Val Thr Gly Glu Tyr Val Arg Ser Thr Val
                        350                 355                 360
            gac ttg atg gca tcg ctg cgt ggg cgc ggc atg gtg ttc gac ggg gtg    1635
            Asp Leu Met Ala Ser Leu Arg Gly Arg Gly Met Val Phe Asp Gly Val
                    365                 370                 375
            tac gtg gtg tcg gac ctt acg cgg ctc ttc gcg gag cta gac ttt ggg    1683
            Tyr Val Val Ser Asp Leu Thr Arg Leu Phe Ala Glu Leu Asp Phe Gly
            380                 385                 390                 395
            cgc ggg gac tgg gtc att agc ggc atg gca cag ccg atg ctg gcg act    1731
            Arg Gly Asp Trp Val Ile Ser Gly Met Ala Gln Pro Met Leu Ala Thr
                                400                 405                 410
            ttc ctg gtg agg tgc agg aac acc gac ggc gag gac gcg gtg gcg gcg    1779
            Phe Leu Val Arg Cys Arg Asn Thr Asp Gly Glu Asp Ala Val Ala Ala
                            415                 420                 425
            tcg atg cta ctg ccg ctc cgg tga tggtgag gtttgcagag gagattgcag       1830
            Ser Met Leu Leu Pro Leu Arg
                        430 ggttgatgac aacgagctcg agctcacgtc tgtagagtat atatgatgaa tcagggttct             1890 gggttcggat tgaaatgttt gaatttcgac gacgaatttc atccatttag gtgacatccg             1950 agagaacatg tcacttcctt ttcgtcttaa cttggttcgt acttggtcag atttatcaaa             2010 tcggatgaaa ttattttct gaaatttaa aaattcatc atttcgatga gccctgaata               2070 tttgttgtgc aatcagatcc tagaaccctg gatgaatatc gtctttacta ttcgagataa             2130 tatataccgt tacatatctt aaatcttttc tttacccatc taacaaattt acaagaagta             2190 aatctcaagc                                                                    2200

<210> SEQ ID NO 14
<211> LENGTH: 434
<212> TYPE: PRT
<213> ORGANISM: Oryza sativa

<400> SEQUENCE: 14

Met Ala Ser Arg Ser Arg Leu Val Ala Arg Arg Ser Lys Pro Glu Leu
1               5                   10                  15

Val Ala Pro Ser Arg Arg Thr Pro His Asp Thr Lys Leu Leu Ser Asp
            20                  25                  30

Leu Asp Asp Phe Arg Asn His Tyr Glu Tyr Thr Pro Leu Val Ala Phe
        35                  40                  45
```

Phe Arg Thr Ser Ser Thr Gly Asn Ile Pro Ser Ala Pro Pro Glu
    50              55              60

Met Thr Ile Arg Arg Ala Ile Ala Glu Ala Leu Val Tyr Tyr Pro
65              70              75              80

Leu Ala Gly Arg Leu Arg Glu Leu Pro Cys Gly Lys Leu Val Asp
                85              90              95

Cys Thr Glu Glu Gly Val Val Phe Val Ala Glu Ala Asp Leu Arg
            100             105             110

Leu Ala Asp Leu Gly Glu Pro Leu Leu Leu Pro Phe Pro Cys Ser Gly
        115             120             125

Glu Leu Leu Val Cys Asp Asn Val Gly Asp Ser Gln Val Ala Val Val
    130             135             140

Ala Lys Pro Leu Ile Phe Met Gln Val Thr Glu Phe Lys Cys Gly Gly
145             150             155             160

Phe Ala Val Ala Met Gln Trp Asn His Cys Val Ala Asp Gly Phe Gly
                165             170             175

Ala Ser Gln Phe Met Asn Ala Ile Ala Asp Leu Ala Arg Gly Glu Pro
            180             185             190

Arg Pro Leu Val Leu Pro Val Trp Glu Arg His Leu Val Met Ala Arg
        195             200             205

Ala Pro Pro Ser Val Ala Ala Ala Tyr Pro Ala Phe Lys Pro Leu Ile
210             215             220

Asp Gly Ala Ser Ser Asn Asp Val Met Leu Ser Thr Pro Leu Asp Thr
225             230             235             240

Met Val Thr Arg His Phe Leu Phe Gly Arg Arg Glu Met Ala Ala Leu
                245             250             255

Arg Arg Leu Leu Pro Ala Pro Leu Gly Arg Arg Cys Thr Asp Phe Gln
            260             265             270

Leu Leu Pro Ala Ala Leu Trp Arg Cys Arg Thr Ala Ala Leu Pro Tyr
        275             280             285

Ala Pro His Arg Arg Val Arg Ala Tyr Leu Pro Leu Ser Thr Arg Gly
    290             295             300

Arg Arg Trp Arg Ser Gln Gly Leu His Ile Pro Glu Gly Tyr Tyr Gly
305             310             315             320

Asn Ala Leu Ala Tyr Ser Ile Ala Asn Ala Ser Ala Gly Asp Leu Cys
                325             330             335

Gly Gly Thr Leu Gly Gln Thr Val Glu Leu Val Cys Glu Ala Arg Leu
            340             345             350

Gln Val Thr Gly Glu Tyr Val Arg Ser Thr Val Asp Leu Met Ala Ser
        355             360             365

Leu Arg Gly Arg Gly Met Val Phe Asp Gly Val Tyr Val Val Ser Asp
    370             375             380

Leu Thr Arg Leu Phe Ala Glu Leu Asp Phe Gly Arg Gly Asp Trp Val
385             390             395             400

Ile Ser Gly Met Ala Gln Pro Met Leu Ala Thr Phe Leu Val Arg Cys
                405             410             415

Arg Asn Thr Asp Gly Glu Asp Ala Val Ala Ala Ser Met Leu Leu Pro
            420             425             430

Leu Arg

<210> SEQ ID NO 15
<211> LENGTH: 1305
<212> TYPE: DNA
<213> ORGANISM: Oryza sativa

<400> SEQUENCE: 15

```
atggcgagtc ggagtaggct ggtggcacgt cggagcaagc ctgagctggt ggcgccgtca        60
cgccgcacgc cgcacgacac caagcttctc tccgacctcg acgatttccg caaccactac       120
gagtacaccc cacttgtcgc cttcttccgc acctccagca ccggcaacat cccgtcggcg       180
ccgccaccgg agatgaccat ccggagagca attgcggagg cgctcgtgta ctactaccca       240
ctagccggcc gcctgcgcga gcttccctgc ggcaagctgg tggtggactg caccgaggaa       300
gggtggtgt cgtcgccgc cgaggctgac ctgcgcctcg ctgacctcgg cgagccactg       360
ctcctgccat tcccgtgctc cggcgagctg ctcgtctgcg acaatgtggg agacagccaa       420
gtcgccgtcg ttgccaagcc attgatcttc atgcaggtga cggaattcaa atgcggagga       480
tttgccgttg ccatgcaatg aaccactgt gtcgccgatg gttttggggc cagccagttc       540
atgaacgcca tcgccgacct cgctcgcggc gagccgcgcc cgctcgtgct ccccgtgtgg       600
gagaggcacc tcgtcatggc gcgcgcgcca cccagcgtcg ccgccgcgta cccggcgttc       660
aagccgctca tcgacggcgc cagcagcaac gacgtgatgc tctccacgcc gcttgacacc       720
atggtgaccc ggcacttcct gttcggccgg cgagagatgc ccgcgctacg gcgcctcctc       780
cccgcacccc tcggcggcg ctgcacggac ttccagctgc tccccgccgc gctatggcgg       840
tgccgcacgg cggcgctgcc ctacgccccg caccggcgag tgcgtgccta cctcccctg        900
agcacgcgcg ggagacggtg gcgcagccag gggctgcaca tcccggaggg gtactacggc       960
aacgcgctcg cctactccat cgccaacgcc agcgccggcg atctgtgcgg cgggacgctg      1020
gggcagacgg tggagctggt ctgcgaggcg aggctacagg tgacgggggga gtacgtgaga      1080
tcgacggtgg acttgatggc atcgctgcgt gggcgcggca tggtgttcga cggggtgtac      1140
gtggtgtcgg accttacgcg gctcttcgcg gagctagact ttgggcgcgg ggactgggtc      1200
attagcggca tggcacagcc gatgctgcg acttttcctgg tgaggtgcag gaacaccgac      1260
ggcgaggacg cggtggcggc gtcgatgcta ctgccgctcc ggtga                      1305
```

<210> SEQ ID NO 16
<211> LENGTH: 5190
<212> TYPE: DNA
<213> ORGANISM: Oryza sativa
<220> FEATURE:
<221> NAME/KEY: CDS
<222> LOCATION: (502)..(960)
<223> OTHER INFORMATION:
<220> FEATURE:
<221> NAME/KEY: Intron
<222> LOCATION: (961)..(3173)
<223> OTHER INFORMATION:
<220> FEATURE:
<221> NAME/KEY: CDS
<222> LOCATION: (3174)..(3232)
<223> OTHER INFORMATION:
<220> FEATURE:
<221> NAME/KEY: Intron
<222> LOCATION: (3233)..(3682)
<223> OTHER INFORMATION:
<220> FEATURE:
<221> NAME/KEY: CDS
<222> LOCATION: (3683)..(3729)
<223> OTHER INFORMATION:
<220> FEATURE:
<221> NAME/KEY: Intron
<222> LOCATION: (3730)..(3866)
<223> OTHER INFORMATION:
<220> FEATURE:
<221> NAME/KEY: CDS
<222> LOCATION: (3867)..(4792)

<223> OTHER INFORMATION:

<400> SEQUENCE: 16

```
agctaggcat ggcttaaaaa ggttctttct aaaattctat gtcctgctgt aaacatatta      60
tcaatatata tagcggagta gtcaaaatac atgcatttga ttacttttag tagttcattt     120
aagtttacat acccgacgat aatatcaagt ggaagctcac atgccgtaag gaatatacaa     180
ttgtttctct atttaattcc atcgacattc ttaataccgt gcctaaacta aaactcctta     240 tatttttttgt gactttgtga agaacaactc atcgattaat taccctgctt aattttttt      300 gaaaggaatg gcctgcttaa tttattatat atatgccgag cggctgagat atagctagct     360
gaattagctg tgagacatag acacagcaag ttttcgttta tcctcctgga actaatatat     420
agccttgcat cgatccatca taggtatact agtactagta cagcatataa ttgtgagtga     480
ccggccatat ggtgattggt g atg aag ata ttt tca gca cgg cgg agc agg         531
                       Met Lys Ile Phe Ser Ala Arg Arg Ser Arg
                         1               5                  10 gca gag ctt gtg gcg cca tca cgg ccg acg cca cgc gac acc aag atc        579
Ala Glu Leu Val Ala Pro Ser Arg Pro Thr Pro Arg Asp Thr Lys Ile
              15                  20                  25 ctc tcc gac ctc gat gat ttc cca aac cac cac gag tac acc cct gta        627
Leu Ser Asp Leu Asp Asp Phe Pro Asn His His Glu Tyr Thr Pro Val
         30                  35                  40 ctc ttc ttc ttc cgc gtc tcc ggt gat gat gac caa ccg ccg cca ccg        675
Leu Phe Phe Phe Arg Val Ser Gly Asp Asp Asp Gln Pro Pro Pro Pro
     45                  50                  55 gat cag acg aag tgg gcg acc acc gtg ttc cgg acg gcg ctt gcc gag        723
Asp Gln Thr Lys Trp Ala Thr Thr Val Phe Arg Thr Ala Leu Ala Glu
 60                  65                  70 gcc ctt gtg tac ttg tac cca atg gct ggg cgg ctg agg atg ctt ccc        771
Ala Leu Val Tyr Leu Tyr Pro Met Ala Gly Arg Leu Arg Met Leu Pro
 75                  80                  85                  90 tcc ggc aag ctg gcg gtg gac tgc acg gag gaa ggg gtg gtg ctg gtg        819
Ser Gly Lys Leu Ala Val Asp Cys Thr Glu Glu Gly Val Val Leu Val
             95                 100                 105 gca gcg gag gct gac ctg cgg ctg gcc gac ctc ggt gag ccg ttg ctg        867
Ala Ala Glu Ala Asp Leu Arg Leu Ala Asp Leu Gly Glu Pro Leu Leu
             110                 115                 120 ccg cca ttt ccg tgc gtc ggc gag ctt gtc tgt cac aat agt att gtg        915
Pro Pro Phe Pro Cys Val Gly Glu Leu Val Cys His Asn Ser Ile Val
         125                 130                 135 gga gac att cgg gtg gtc ctt ggg aag ccc ctc gtc ttc ctg cag            960
Gly Asp Ile Arg Val Val Leu Gly Lys Pro Leu Val Phe Leu Gln
 140                 145                 150 gtatcttctt cgatttttta atacacacat gacacatgca tgtttaatta ttaatatttt    1020
tcttccttta aaataatgca taactattat taatttcatt gtgatttatt ttataattaa    1080
acatatactt ttagtattac tttttttac atatttttaa taagaatgat agctgtatgt    1140 ttaaaatca acatagctaa aaaaaataat actatgtagt actatgactt ggttgtttc      1200 aaaattaaac taaccaaaat aaaaaaaaag tttggaggga gtagcaccct ttgagttgca    1260
aattgatttt tcacaacaaa catattatca cggacggtga atcttaact acttaaaaaa    1320 aattcggtaa ctttcagatc ccacaatttt ttcgtccata taagtccgac tgagtggcat    1380
cctccgtctc caactctcca catgaccacc gaacacaacc acaccgttaa cgcccaaatc    1440
ccaaacataa tatatatgcg aaactcttag tgggcaattg atcgccggcg atcgattccc    1500 ctccccctccc ccccggtcct ctacgtggtt ttctttttg gcaccgcatt attttcctat    1560
```

```
tttagtaaat ttatgcacct aaattttcta cacctcaagt ttatacatgt aaagtttata    1620
tatccgattc aaatttgaat tgaattcaa atatttttta tatatagtat ttctatatat    1680
ctaaagttta tacacctaaa gtttatagac ccaaagttta tacccgat tcaaatttga    1740 atttgaattc aaatatttt aatataatat tctatacatc taaagtttat agacccaaag    1800
tttataagtc aaaagtttac atacccgatt caaatttgaa tttgaattat attcgattca    1860
aatttgaatt tgaattcaaa tatttttata tatagtattt ctatacatct aaagtttata    1920
gacccaaagt ttataagtca aaagtttaca tacccgattc aaatttgaat ttgaattata    1980
ttcgattcaa atttgaattt gaattcaaat attttatat atagtatttc tatacttcta    2040
aagtttatac acctaagtt tatagaccaa agtttataa gtcaaaagtt tacatacccca    2100 attcaaattt gaatttgaat tcaaatatta gtttatagac ccaaagttta taagtcaaaa    2160
gtttacatac tcgtttcaaa tttgaatttg aattcaaata tttttatat atagtatttc    2220 tatacataaa tttttccaac tttgttgttt attatttttt tagaaaatct attatattgt    2280
taaaggatta gaaaaaggag cctccacgtt cgctctcatg gtctagaaat tctcacatta    2340
atcggagaaa aagaaaaggc agagtccata tagaaatata atttagaaat agctgaaatt    2400
cggaattaaa aaataaggaa tattagaaga ggagactaga gtccatatag aaatataatt    2460
tagaaatagt tgaaattcgg aattaaaaaa taaggaatat agaagtata ttatagagtc    2520 catatccata tagaaataca attagaaaat aatataaatt cggaattaaa aataaggaat    2580
attataagta gagtatagag tccatataaa aatacaatta agaaaaaaat cggaattaaa    2640
aaataaggaa tattagaagt agagtttaga atccgtttaa aaattcaatt tactaaaatt    2700
cgagattaag aaaaacatgg gaagaagagt ttaaagtcaa tataggaata aaatttacaa    2760
gtaactgaaa ttcgaaatta aaaattaaaa aatattgaaa ggtgagttta gagaccacat    2820
agaaatacaa tttgaaataa taaaaattca gaaataaaaa taataatat tagaagaaga    2880 gcctagagtc tatatagaaa taaatttaca gaaaattcgg aattaaaaaa taaatattaa    2940
aagatgagtc tagagtccat ataggaatat atataattta caaataacta aaatttgata    3000
ttaaaaataa ttataaaata caatatgaat attatacatt agtagtttcg taaagttatt    3060
gcaaaattta aaattatgtt gtcattttaa tatatttgaa taatatattg agaaaacata    3120
tatgatatta tatgagagaa aatataatga tgctagttgc gcaatctgta cag gcc       3176
                                                               Ala acc atg cta gtt tat agt aaa gta gga aga gaa gaa cgg agc gga agg     3224
Thr Met Leu Val Tyr Ser Lys Val Gly Arg Glu Glu Arg Ser Gly Arg
155                 160                 165                 170 gag gag ag  gtatgtacag cgtacatggg gcatggggat cgatcgagcg             3272
Glu Glu Arg atcgtccatt agccgtcccc atatatatgt cccaccaaac acttaggtcg gaagtcaaag    3332
cacatctgac cgtgaagaat ttgaagtttc agtagatcgg aagaagaacc aaacaaaaca    3392
aatatcatag tttgaagatt ccaaaaaaaa tagcaggctc ggctccgatg catgtagtaa    3452
aaaaatgaaa aataatccag gcacaaatta tacagactaa atcacaaagt ttggcacagc    3512
taaacaaatt ccaacattcc tccagttaaa atctactccc tctatttcga aatatttgac    3572
gccgttgact tttgtaaaca tgtttgacca ttcgtcttat ttaaaaaatt taagtaatta    3632
ttacatcttt tcttatcatt tgattcattg ttaaatatat ttttatgtag g cat ata    3689
                                                          His Ile
                                                          175
```

```
att tta cat att tca caa aag ttt ttg aat aag acg aac g gtcaaacata       3739
Ile Leu His Ile Ser Gln Lys Phe Leu Asn Lys Thr Asn
                180                 185 tactaaaaag tcaacggtgt taaacatttc gaacggagag agtattacac atatcattta     3799
ggtaagttta aatatatttc actgaagtaa attgttggag agtggacata ttaatctttt     3859 tgtgtag tg acg gaa ttc aaa tgc gga gga ttt gct att ggt ctc cac         3907
        Val Thr Glu Phe Lys Cys Gly Gly Phe Ala Ile Gly Leu His
            190                 195                 200 atg aac cac tgc ata gcc gac ggc ttt ggc ctc acc ctg ttt gtg aaa        3955
Met Asn His Cys Ile Ala Asp Gly Phe Gly Leu Thr Leu Phe Val Lys
            205                 210                 215 gcc atc gcc gat ctc gcc tgt ggc gag cca cgc ccg ctc gcg ctc ccg        4003
Ala Ile Ala Asp Leu Ala Cys Gly Glu Pro Arg Pro Leu Ala Leu Pro
220                 225                 230 gtg tgg gag agg cac ctc ctc atg gtc cgc gcg cca ccc agc gtc gcc        4051
Val Trp Glu Arg His Leu Leu Met Val Arg Ala Pro Pro Ser Val Ala
235                 240                 245                 250 gcc gcg tac ccg gcg ttc aag ccg ctc atc gac ggc gcc agc agc            4099
Ala Ala Tyr Pro Ala Phe Lys Pro Leu Ile Asp Gly Gly Ala Ser Ser
                255                 260                 265 ggc gat gac gac gtg atg ctc acc acg ccg ctt gac acc atg gtg acc        4147
Gly Asp Asp Asp Val Met Leu Thr Thr Pro Leu Asp Thr Met Val Thr
            270                 275                 280 cgg cac ttc ctc ttc ggc cgg cga gag atg gcc gcg cta cgg cgc cac        4195
Arg His Phe Leu Phe Gly Arg Arg Glu Met Ala Ala Leu Arg Arg His
            285                 290                 295 ctc ccc gca cac ctc agc cgg cgg tgc acg gac ttt gag ctg ctc gcc        4243
Leu Pro Ala His Leu Ser Arg Arg Cys Thr Asp Phe Glu Leu Leu Ala
300                 305                 310 gcc gtg ctg tgg cgg tgc cgc acg gcg gcg ctc ttc tac gct cct cac        4291
Ala Val Leu Trp Arg Cys Arg Thr Ala Ala Leu Phe Tyr Ala Pro His
315                 320                 325                 330 cgg cag gtg tgt ctc tac ctc ccg tcg aac gcg cgt ggc aga cgg atg        4339
Arg Gln Val Cys Leu Tyr Leu Pro Ser Asn Ala Arg Gly Arg Arg Met
                335                 340                 345 cgg cgc cgc cac ggc gtg cac gtc ccg gag ggg tac tac agc aac gcg        4387
Arg Arg Arg His Gly Val His Val Pro Glu Gly Tyr Tyr Ser Asn Ala
            350                 355                 360 ctc gcc tac act atc gtc cac gcc agc gcc ggc gag cta tgt ggc ggc        4435
Leu Ala Tyr Thr Ile Val His Ala Ser Ala Gly Glu Leu Cys Gly Gly
            365                 370                 375 acg ttg ggt cac act gtg gag gtc gtc tgc gag gcc aag ctc cgg atg        4483
Thr Leu Gly His Thr Val Glu Val Val Cys Glu Ala Lys Leu Arg Met
380                 385                 390 acg gag gag tac gtg aga tcg acg gtg gat ttg ctg gtg tcg ctg cgt        4531
Thr Glu Glu Tyr Val Arg Ser Thr Val Asp Leu Leu Val Ser Leu Arg
395                 400                 405                 410 cag cgt ggg cgc gcc ctg gtg ttc gac ggt gtg ttt gtg gtg tcg gac        4579
Gln Arg Gly Arg Ala Leu Val Phe Asp Gly Val Phe Val Val Ser Asp
                415                 420                 425 gcg acg cgc ctc gtc ggg gag cta gac ttt gga cgc ggc ggg gag tgg        4627
Ala Thr Arg Leu Val Gly Glu Leu Asp Phe Gly Arg Gly Gly Glu Trp
            430                 435                 440 gtc ggc gcc ggc gtt gcg cag ccg atg cgg gcg acg ttc ctc gtg agg        4675
Val Gly Ala Gly Val Ala Gln Pro Met Arg Ala Thr Phe Leu Val Arg
            445                 450                 455 tgc agg gat gcc gac ggc gaa gac gcg gtg gcg gcg tcg atg ctg ttg        4723
Cys Arg Asp Ala Asp Gly Glu Asp Ala Val Ala Ala Ser Met Leu Leu
460                 465                 470
```

-continued

```
cca cct ccg gcg atg gac aag ttt gca gag gac att gca gaa gcg ttg      4771
Pro Pro Pro Ala Met Asp Lys Phe Ala Glu Asp Ile Ala Glu Ala Leu
475                 480                 485                 490 ctc atc acc tcc cgg ctg tag atggatt atagtaatta tatcgatcca            4819
Leu Ile Thr Ser Arg Leu
                495 tggagtcttt gtgtttgtct cgtgcatgct ttattaatca ctagaaataa tggctgcgtt    4879 gtaacgggta atattatttt taatcttatt attgttatac agtttaatta aggtgaaatt    4939 caatatgaga attcgcttgg atatatatat atatttttg aaaatcatga actgcaatta     4999 gaatttcgat catctcaagt tagcatgcaa aatttttttaa agagatttct tatatgactc   5059 attctgtttt tctaaaagcg aacaaattta aaacccgact caaatacgga tatacatttc    5119 taaaagcgaa cgaacttaaa aaccgattta tacatagata acgtaccaaa gtaccgacaa    5179 aaatatcttc a                                                         5190
```

<210> SEQ ID NO 17
<211> LENGTH: 496
<212> TYPE: PRT
<213> ORGANISM: Oryza sativa

<400> SEQUENCE: 17

```
Met Lys Ile Phe Ser Ala Arg Arg Ser Arg Ala Glu Leu Val Ala Pro
1               5                   10                  15

Ser Arg Pro Thr Pro Arg Asp Thr Lys Ile Leu Ser Asp Leu Asp Asp
            20                  25                  30

Phe Pro Asn His His Glu Tyr Thr Pro Val Leu Phe Phe Phe Arg Val
        35                  40                  45

Ser Gly Asp Asp Asp Gln Pro Pro Pro Asp Gln Thr Lys Trp Ala
    50                  55                  60

Thr Thr Val Phe Arg Thr Ala Leu Ala Glu Ala Leu Val Tyr Leu Tyr
65                  70                  75                  80

Pro Met Ala Gly Arg Leu Arg Met Leu Pro Ser Gly Lys Leu Ala Val
                85                  90                  95

Asp Cys Thr Glu Glu Gly Val Val Leu Val Ala Ala Glu Ala Asp Leu
            100                 105                 110

Arg Leu Ala Asp Leu Gly Glu Pro Leu Leu Pro Pro Phe Pro Cys Val
        115                 120                 125

Gly Glu Leu Val Cys His Asn Ser Ile Val Gly Asp Ile Arg Val Val
    130                 135                 140

Leu Gly Lys Pro Leu Val Phe Leu Gln Ala Thr Met Leu Val Tyr Ser
145                 150                 155                 160

Lys Val Gly Arg Glu Glu Arg Ser Gly Arg Glu Arg His Ile Ile
                165                 170                 175

Leu His Ile Ser Gln Lys Phe Leu Asn Lys Thr Asn Val Thr Glu Phe
            180                 185                 190

Lys Cys Gly Gly Phe Ala Ile Gly Leu His Met Asn His Cys Ile Ala
        195                 200                 205

Asp Gly Phe Gly Leu Thr Leu Phe Val Lys Ala Ile Ala Asp Leu Ala
    210                 215                 220

Cys Gly Glu Pro Arg Pro Leu Ala Leu Pro Val Trp Glu Arg His Leu
225                 230                 235                 240

Leu Met Val Arg Ala Pro Pro Ser Val Ala Ala Tyr Pro Ala Phe
                245                 250                 255
```

```
Lys Pro Leu Ile Asp Gly Gly Ala Ser Ser Gly Asp Asp Val Met
            260                 265                 270

Leu Thr Thr Pro Leu Asp Thr Met Val Thr Arg His Phe Leu Phe Gly
        275                 280                 285

Arg Arg Glu Met Ala Ala Leu Arg Arg His Leu Pro Ala His Leu Ser
    290                 295                 300

Arg Arg Cys Thr Asp Phe Glu Leu Leu Ala Ala Val Leu Trp Arg Cys
305                 310                 315                 320

Arg Thr Ala Ala Leu Phe Tyr Ala Pro His Arg Gln Val Cys Leu Tyr
                325                 330                 335

Leu Pro Ser Asn Ala Arg Gly Arg Met Arg Arg His Gly Val
            340                 345                 350

His Val Pro Glu Gly Tyr Tyr Ser Asn Ala Leu Ala Tyr Thr Ile Val
        355                 360                 365

His Ala Ser Ala Gly Glu Leu Cys Gly Gly Thr Leu Gly His Thr Val
    370                 375                 380

Glu Val Val Cys Glu Ala Lys Leu Arg Met Thr Glu Glu Tyr Val Arg
385                 390                 395                 400

Ser Thr Val Asp Leu Leu Val Ser Leu Arg Gln Arg Gly Arg Ala Leu
                405                 410                 415

Val Phe Asp Gly Val Phe Val Val Ser Asp Ala Thr Arg Leu Val Gly
            420                 425                 430

Glu Leu Asp Phe Gly Arg Gly Gly Glu Trp Val Gly Ala Gly Val Ala
        435                 440                 445

Gln Pro Met Arg Ala Thr Phe Leu Val Arg Cys Arg Asp Ala Asp Gly
    450                 455                 460

Glu Asp Ala Val Ala Ala Ser Met Leu Leu Pro Pro Ala Met Asp
465                 470                 475                 480

Lys Phe Ala Glu Asp Ile Ala Glu Ala Leu Leu Ile Thr Ser Arg Leu
                485                 490                 495

<210> SEQ ID NO 18
<211> LENGTH: 1491
<212> TYPE: DNA
<213> ORGANISM: Oryza sativa

<400> SEQUENCE: 18
atgaagatat tttcagcacg gcggagcagg gcagagcttg tggcgccatc acggccgacg      60
ccacgcgaca ccaagatcct ctccgacctc gatgatttcc caaaccacca cgagtacacc     120
cctgtactct tcttcttccg cgtctccggt gatgatgacc aaccgccgcc accggatcag     180
acgaagtggg cgaccaccgt gttccggacg gcgcttgccg aggcccttgt gtacttgtac     240
ccaatggctg gcggctgag gatgcttccc tccggcaagc tggcggtgga ctgcacggag     300 gaagggggtgg tgctggtggc agcggaggct gacctgcggc tggccgacct cggtgagccg     360
ttgctgccgc catttccgtg cgtcggcgag cttgtctgtc acaatagtat tgtgggagac     420
attcgggtgg tccttgggaa gccccctcgtc ttcctgcagg ccaccatgct agtttatagt     480
aaagtaggaa gagaagaacg gagcggaagg gaggagaggc atataatttt acatatttca     540
caaaagtttt tgaataagac gaacgtgacg gaattcaaat gcggaggatt tgctattggt     600
ctccacatga accactgcat agccgacggc tttggcctca ccctgtttgt gaaagccatc     660
gccgatctcg cctgtggcga gccacgcccg ctcgcgctcc cggtgtggga gaggcacctc     720
ctcatggtcc gcgcgccacc cagcgtcgcc gccgcgtacc cggcgttcaa gccgctcatc     780
```

-continued

```
gacggcggcg ccagcagcgg cgatgacgac gtgatgctca ccacgccgct tgacaccatg    840
gtgacccggc acttcctctt cggccggcga gagatggccg cgctacggcg ccacctcccc    900
gcacacctca gccggcggtg cacggactttt gagctgctcg ccgccgtgct gtggcggtgc    960
cgcacggcgg cgctcttcta cgctcctcac cggcaggtgt gtctctacct cccgtcgaac   1020
gcgcgtggca gacggatgcg gcgccgccac ggcgtgcacg tcccggaggg gtactacagc   1080
aacgcgctcg cctacactat cgtccacgcc agcgccggcg agctatgtgg cggcacgttg   1140
ggtcacactg tggaggtcgt ctgcgaggcc aagctccgga tgacggagga gtacgtgaga   1200
tcgacggtgg atttgctggt gtcgctgcgc agcgtgggc gcgccctggt gttcgacggt   1260
gtgtttgtgg tgtcggacgc gacgcgcctc gtcggggagc tagactttgg acgcggcggg   1320
gagtgggtcg gcgccggcgt tgcgcagccg atgcgggcga cgttcctcgt gaggtgcagg   1380
gatgccgacg gcgaagacgc ggtggcggcg tcgatgctgt tgccacctcc ggcgatggac   1440
aagtttgcag aggacattgc agaagcgttg ctcatcacct cccggctgta g            1491
```

<210> SEQ ID NO 19
<211> LENGTH: 2020
<212> TYPE: DNA
<213> ORGANISM: Oryza sativa
<220> FEATURE:
<221> NAME/KEY: CDS
<222> LOCATION: (497)..(940)
<223> OTHER INFORMATION:
<220> FEATURE:
<221> NAME/KEY: Intron
<222> LOCATION: (941)..(1083)
<223> OTHER INFORMATION:
<220> FEATURE:
<221> NAME/KEY: CDS
<222> LOCATION: (1084)..(1623)
<223> OTHER INFORMATION:

<400> SEQUENCE: 19

```
attgtcgttg caaatatgtc tttttgaaga tatttgctcc agtccaacaa aaagtacctc     60
gaggtattgg tatctgacgg taccaatcgt ttccgatcgt tggatctagc tagtcaagat    120
gggcattgtt agatctaatg atcagaattg atttggtact gtgaggtacc agttcgaggt    180 acttttttgct ggatcaaagc aaatctcctt tttgaaagtt actggttaaa atccagagtt    240
tacgagaatg aattaattag tataagtaaa gatgaaagaa agctatatat atctggctgc    300
tactatatct ggtatatatg aaagaaagtt gaacaaataa aataaaagat ctatccacac    360
atggttgcac cagatcgaaa tggatggata tctatagaaa taattcatta cataacatag    420
cgatcgacca tctaaaacca agtataccac cacattggtt ataagctatt ccattcaagt    480
gcaaggtagt acagcc atg gtc acc ttc aag gca aac cgg agc gat cct gag    532
              Met Val Thr Phe Lys Ala Asn Arg Ser Asp Pro Glu
                1               5                  10 cta gtg cca ccg gca ttg gca aca cct cga gag atg aag gcc ctc tct    580
Leu Val Pro Pro Ala Leu Ala Thr Pro Arg Glu Met Lys Ala Leu Ser
         15                  20                  25 gat gtt gac acc caa cct gct cta cgc ttc tat gcc acc gga gtg gag    628
Asp Val Asp Thr Gln Pro Ala Leu Arg Phe Tyr Ala Thr Gly Val Glu
     30                  35                  40 ttc ttc cgc cat cac ccc att gtc gac gac ggc cat gat cag ccg gag    676
Phe Phe Arg His His Pro Ile Val Asp Asp Gly His Asp Gln Pro Glu
45                  50                  55                  60 aac caa gcc aag gtt gtc aag gat gct gtt gca aag gcg ctc aca tac    724
Asn Gln Ala Lys Val Val Lys Asp Ala Val Ala Lys Ala Leu Thr Tyr
                 65                  70                  75
```

```
ttc tac ccg gtg gct ggt cga atc cgt gag ctc ccc gga ggg gag ttg        772
Phe Tyr Pro Val Ala Gly Arg Ile Arg Glu Leu Pro Gly Gly Glu Leu
             80                  85                  90 gtt gtg gag tgc act gga gaa ggg gtg gtt ttt gtt gag gcc gac gct        820
Val Val Glu Cys Thr Gly Glu Gly Val Val Phe Val Glu Ala Asp Ala
         95                 100                 105 gat gtg tgg ttg gat gag ttt ggg aat ccc atc atg cca cca tat cca        868
Asp Val Trp Leu Asp Glu Phe Gly Asn Pro Ile Met Pro Pro Tyr Pro
    110                 115                 120 tgc gtc gac gag ttc ttg tgt gac cct ggt gac act agt gtc atc att        916
Cys Val Asp Glu Phe Leu Cys Asp Pro Gly Asp Thr Ser Val Ile Ile
125                 130                 135                 140 ggc aag ccc ctg gtt ttc atg cag gttagcagca aaatcttctc aaagtagaac       970
Gly Lys Pro Leu Val Phe Met Gln
                145 tgaaatgtgt ggcttagtta attctcttac agcaacttgt aattaagatc attgattatg     1030 atacaattaa tgcatatata acatccattc tacatatata taaatatgtg cag gtg        1086
                                                           Val act agg ctc aaa tgt ggc gga ttt gtt atc ggc act tac tca tgc cac       1134
Thr Arg Leu Lys Cys Gly Gly Phe Val Ile Gly Thr Tyr Ser Cys His
150                 155                 160                 165 aac att gtg gat gcc ttt ggc cac acc caa ttt ctg aaa gct ata gtc       1182
Asn Ile Val Asp Ala Phe Gly His Thr Gln Phe Leu Lys Ala Ile Val
                170                 175                 180 gac ata gca cgt ggt gat gat cac cca act gtt ctt cct gtg tgg gga       1230
Asp Ile Ala Arg Gly Asp Asp His Pro Thr Val Leu Pro Val Trp Gly
            185                 190                 195 aga gag ctt atg gca gcg cgt aac cca ccc aat gtt tca ctc ctg cag       1278
Arg Glu Leu Met Ala Ala Arg Asn Pro Pro Asn Val Ser Leu Leu Gln
        200                 205                 210 cac ttg aca cca agc aag cta tcc cca gat cac cca gta gag ccc aat       1326
His Leu Thr Pro Ser Lys Leu Ser Pro Asp His Pro Val Glu Pro Asn
    215                 220                 225 tcg gca gca caa cat gtg tcg tcg tcg aca gat cat atg gtt ggc gac       1374
Ser Ala Ala Gln His Val Ser Ser Ser Thr Asp His Met Val Gly Asp
230                 235                 240                 245 tac ttc ttc ttc ggc cca aga gag att gca gct ctg caa cac cat gcc       1422
Tyr Phe Phe Phe Gly Pro Arg Glu Ile Ala Ala Leu Gln His His Ala
                250                 255                 260 caa ctg cag tac tca agc aca gca ttt gag gtc atc aca gct gca atg       1470
Gln Leu Gln Tyr Ser Ser Thr Ala Phe Glu Val Ile Thr Ala Ala Met
            265                 270                 275 tgg aag tgt cac aca gta gct ctc ggg tat gtg ccg gac cag aat aag       1518
Trp Lys Cys His Thr Val Ala Leu Gly Tyr Val Pro Asp Gln Asn Lys
        280                 285                 290 aag gca tgc ttg ttg atg acc atg aac gct cgt ggg aag tgg aag cgt       1566
Lys Ala Cys Leu Leu Met Thr Met Asn Ala Arg Gly Lys Trp Lys Arg
    295                 300                 305 gat cca cct tta ccg caa gga ttc tac ggc aac gga ttc gtc tac ctt       1614
Asp Pro Pro Leu Pro Gln Gly Phe Tyr Gly Asn Gly Phe Val Tyr Leu
310                 315                 320                 325 gtt gtg tag acggacg ctagtgagct atgcaagcag tcgctaggcc atgcggtgaa       1670
Val Val gcttgtccag aaggccaagc ttgatatgac cgaagaattc acaaaatcaa tggtggattt     1730
catcgcactt catggaggac caccatatgt ggcaggatgg atgtttgtgg tgtctgatat     1790
aacacgtata ggagaagatg ccttggactt tggttgggct caacgggttg ctggtggtgt     1850
```

```
gccaatggtc ggagatgtca aatgtaagca agtgagttat cagatgagat gcatcaatga      1910
cagtggtgag gattgtgttg tggcatccat gttcttacca aaatcagcca tggagatatt      1970
tgccaaggag atcttggtgt tgtcgtctaa ggagattgaa taaatcaacc                 2020
```

<210> SEQ ID NO 20
<211> LENGTH: 327
<212> TYPE: PRT
<213> ORGANISM: Oryza sativa

<400> SEQUENCE: 20

```
Met Val Thr Phe Lys Ala Asn Arg Ser Asp Pro Glu Leu Val Pro Pro
1               5                   10                  15

Ala Leu Ala Thr Pro Arg Glu Met Lys Ala Leu Ser Asp Val Asp Thr
            20                  25                  30

Gln Pro Ala Leu Arg Phe Tyr Ala Thr Gly Val Glu Phe Phe Arg His
        35                  40                  45

His Pro Ile Val Asp Asp Gly His Asp Gln Pro Glu Asn Gln Ala Lys
    50                  55                  60

Val Val Lys Asp Ala Val Ala Lys Ala Leu Thr Tyr Phe Tyr Pro Val
65                  70                  75                  80

Ala Gly Arg Ile Arg Glu Leu Pro Gly Gly Glu Leu Val Val Glu Cys
                85                  90                  95

Thr Gly Glu Gly Val Val Phe Val Glu Ala Asp Ala Asp Val Trp Leu
            100                 105                 110

Asp Glu Phe Gly Asn Pro Ile Met Pro Pro Tyr Pro Cys Val Asp Glu
        115                 120                 125

Phe Leu Cys Asp Pro Gly Asp Thr Ser Val Ile Ile Gly Lys Pro Leu
130                 135                 140

Val Phe Met Gln Val Thr Arg Leu Lys Cys Gly Gly Phe Val Ile Gly
145                 150                 155                 160

Thr Tyr Ser Cys His Asn Ile Val Asp Ala Phe Gly His Thr Gln Phe
                165                 170                 175

Leu Lys Ala Ile Val Asp Ile Ala Arg Gly Asp Asp His Pro Thr Val
            180                 185                 190

Leu Pro Val Trp Gly Arg Glu Leu Met Ala Ala Arg Asn Pro Pro Asn
        195                 200                 205

Val Ser Leu Leu Gln His Leu Thr Pro Ser Lys Leu Ser Pro Asp His
210                 215                 220

Pro Val Glu Pro Asn Ser Ala Ala Gln His Val Ser Ser Ser Thr Asp
225                 230                 235                 240

His Met Val Gly Asp Tyr Phe Phe Gly Pro Arg Glu Ile Ala Ala
                245                 250                 255

Leu Gln His His Ala Gln Leu Gln Tyr Ser Ser Thr Ala Phe Glu Val
            260                 265                 270

Ile Thr Ala Ala Met Trp Lys Cys His Thr Val Ala Leu Gly Tyr Val
        275                 280                 285

Pro Asp Gln Asn Lys Lys Ala Cys Leu Leu Met Thr Met Asn Ala Arg
    290                 295                 300

Gly Lys Trp Lys Arg Asp Pro Pro Leu Pro Gln Gly Phe Tyr Gly Asn
305                 310                 315                 320

Gly Phe Val Tyr Leu Val Val
                325
```

<210> SEQ ID NO 21

```
<211> LENGTH: 984
<212> TYPE: DNA
<213> ORGANISM: Oryza sativa

<400> SEQUENCE: 21
atggtcacct tcaaggcaaa ccggagcgat cctgagctag tgccaccggc attggcaaca        60
cctcgagaga tgaaggccct ctctgatgtt gacacccaac ctgctctacg cttctatgcc       120
accggagtgg agttcttccg ccatcacccc attgtcgacg acggccatga tcagccggag       180
aaccaagcca aggttgtcaa ggatgctgtt gcaaggcgc tcacatactt ctacccggtg        240
gctggtcgaa tccgtgagct ccccggaggg gagttggttg tggagtgcac tggagaaggg       300
gtggtttttg ttgaggccga cgctgatgtg tggttggatg agtttgggaa tcccatcatg       360
ccaccatatc catgcgtcga cgagttcttg tgtgaccctg gtgacactag tgtcatcatt       420
ggcaagcccc tggttttcat gcaggtgact aggctcaaat gtggcggatt tgttatcggc       480
acttactcat gccacaacat tgtggatgcc tttggccaca cccaatttct gaaagctata       540
gtcgacatag cacgtggtga tgatcaccca actgttcttc ctgtgtgggg aagagagctt       600
atggcagcgc gtaacccacc caatgtttca ctcctgcagc acttgacacc aagcaagcta       660
tccccagatc acccagtaga gcccaattcg gcagcacaac atgtgtcgtc gtcgacagat       720
catatggttg gcgactactt cttcttcggc ccaagagaga ttgcagctct gcaacaccat       780
gcccaactgc agtactcaag cacagcattt gaggtcatca cagctgcaat gtggaagtgt       840
cacacagtag ctctcgggta tgtgccggac cagaataaga aggcatgctt gttgatgacc       900
atgaacgctc gtgggaagtg gaagcgtgat ccacctttac cgcaaggatt ctacggcaac       960
ggattcgtct accttgttgt gtag                                              984
```